United States Patent
Marsh

(10) Patent No.: US 10,344,753 B2
(45) Date of Patent: Jul. 9, 2019

(54) MICRO PUMP SYSTEMS

(71) Applicant: Stephen Alan Marsh, Carlisle, MA (US)

(72) Inventor: Stephen Alan Marsh, Carlisle, MA (US)

(73) Assignee: Encite LLC, Burlington, MA (US)

( * ) Notice: Subject to any disclaimer, the term of this patent is extended or adjusted under 35 U.S.C. 154(b) by 887 days.

(21) Appl. No.: 14/632,423

(22) Filed: Feb. 26, 2015

(65) Prior Publication Data
US 2015/0267695 A1    Sep. 24, 2015

Related U.S. Application Data

(60) Provisional application No. 61/945,973, filed on Feb. 28, 2014.

(51) Int. Cl.
| | |
|---|---|
| *F04B 45/047* | (2006.01) |
| *A61M 16/06* | (2006.01) |
| *A61M 16/20* | (2006.01) |
| *F04B 45/04* | (2006.01) |
| *A61M 16/00* | (2006.01) |
| *F16K 1/18* | (2006.01) |

(52) U.S. Cl.
CPC ....... *F04B 45/047* (2013.01); *A61M 16/0057* (2013.01); *A61M 16/0666* (2013.01); *A61M 16/20* (2013.01); *F04B 45/043* (2013.01); *F16K 1/18* (2013.01); *A61M 2205/8206* (2013.01)

(58) Field of Classification Search
CPC . F04B 45/047; F04B 45/043; A61M 16/0057; A61M 16/20; A61M 2205/8206; F16K 1/18
See application file for complete search history.

(56) References Cited

U.S. PATENT DOCUMENTS

| | | | |
|---|---|---|---|
| 5,687,767 A | 11/1997 | Bowers | |
| 5,836,750 A | 11/1998 | Cabuz | |
| 6,106,245 A | 8/2000 | Cabuz | |
| 6,179,586 B1 * | 1/2001 | Herb | F04B 43/043 417/322 |

(Continued)

FOREIGN PATENT DOCUMENTS

| | | |
|---|---|---|
| CN | 1338031 | 2/2002 |
| CN | 100402850 | 7/2008 |

(Continued)

OTHER PUBLICATIONS

European Search Report, PCT/US2015/017973.

(Continued)

*Primary Examiner* — Gregory A Anderson
*Assistant Examiner* — Jonathan S Paciorek
(74) *Attorney, Agent, or Firm* — Fish & Richardson P.C.

(57) ABSTRACT

Discloses is a micro-pump that includes a pump body having a compartmentalized pump chamber, with plural inlet and outlet ports and a plurality of membranes disposed in the pump chamber to provide compartments. The membranes are anchored between opposing walls of the pump body and carry electrodes disposed on opposing surfaces of the membranes and walls of the pump body. Also discloses are applications of the micro-pump including as a heat remover and a self-contained continuous positive airway pressure breathing device.

39 Claims, 24 Drawing Sheets

(56) References Cited

U.S. PATENT DOCUMENTS

| | | | |
|---|---|---|---|
| 6,247,908 B1* | 6/2001 | Shinohara | F04B 43/046 417/413.2 |
| 6,261,066 B1* | 7/2001 | Linnemann | F04B 43/043 417/413.1 |
| 6,443,154 B1* | 9/2002 | Jalde | A61M 16/20 128/201.28 |
| 6,568,286 B1* | 5/2003 | Cabuz | F04B 43/043 73/863.31 |
| 6,582,286 B2 | 6/2003 | Minami et al. | |
| 6,758,107 B2 | 7/2004 | Cabuz | |
| 6,889,567 B2 | 5/2005 | Cabuz | |
| 7,090,471 B2 | 8/2006 | Xie et al. | |
| 7,802,970 B2* | 9/2010 | Singhal | F04B 43/043 417/410.2 |
| 2002/0029814 A1 | 3/2002 | Unger | |
| 2003/0068231 A1 | 4/2003 | Cabuz et al. | |
| 2003/0106799 A1 | 6/2003 | Covington et al. | |
| 2003/0231967 A1 | 12/2003 | Najafi et al. | |
| 2004/0103899 A1* | 6/2004 | Noble | A61M 16/01 128/207.18 |
| 2004/0115068 A1* | 6/2004 | Hansen | A61M 5/14224 417/379 |
| 2009/0074595 A1 | 3/2009 | Chen et al. | |
| 2009/0129952 A1 | 5/2009 | Patrascu et al. | |
| 2009/0130607 A1 | 5/2009 | Slafer | |
| 2010/0181871 A1 | 7/2010 | Daniel et al. | |
| 2011/0207328 A1 | 8/2011 | Speakman | |
| 2014/0147346 A1 | 5/2014 | Chitnis et al. | |
| 2016/0131126 A1 | 5/2016 | Marsh | |

FOREIGN PATENT DOCUMENTS

| | | |
|---|---|---|
| CN | 101389200 | 3/2009 |
| CN | 101526078 | 9/2009 |
| SU | 1756618 | 8/1992 |
| WO | WO2009/094572 A1 | 7/2009 |
| WO | WO 2013/046330 | 4/2013 |
| WO | WO2014/016562 | 1/2014 |

OTHER PUBLICATIONS

PCT International Search Report & Written Opinion (PCT/US2015/017973).
http://www.murata-ps.com/emena/2012-05-22.html 2 pages.
PCT/US15/17973 Int'l Search Report and Written Opinion.
Search Report, China.
Examination Report, IP Australia.
JP Official Action, Japanese Patent Application 2016-572361, dated Jan. 4, 2019, 64 pgs.
OA & Search Report, Chinese Application No. 201580067081X, dated Jun. 27, 2018.

* cited by examiner

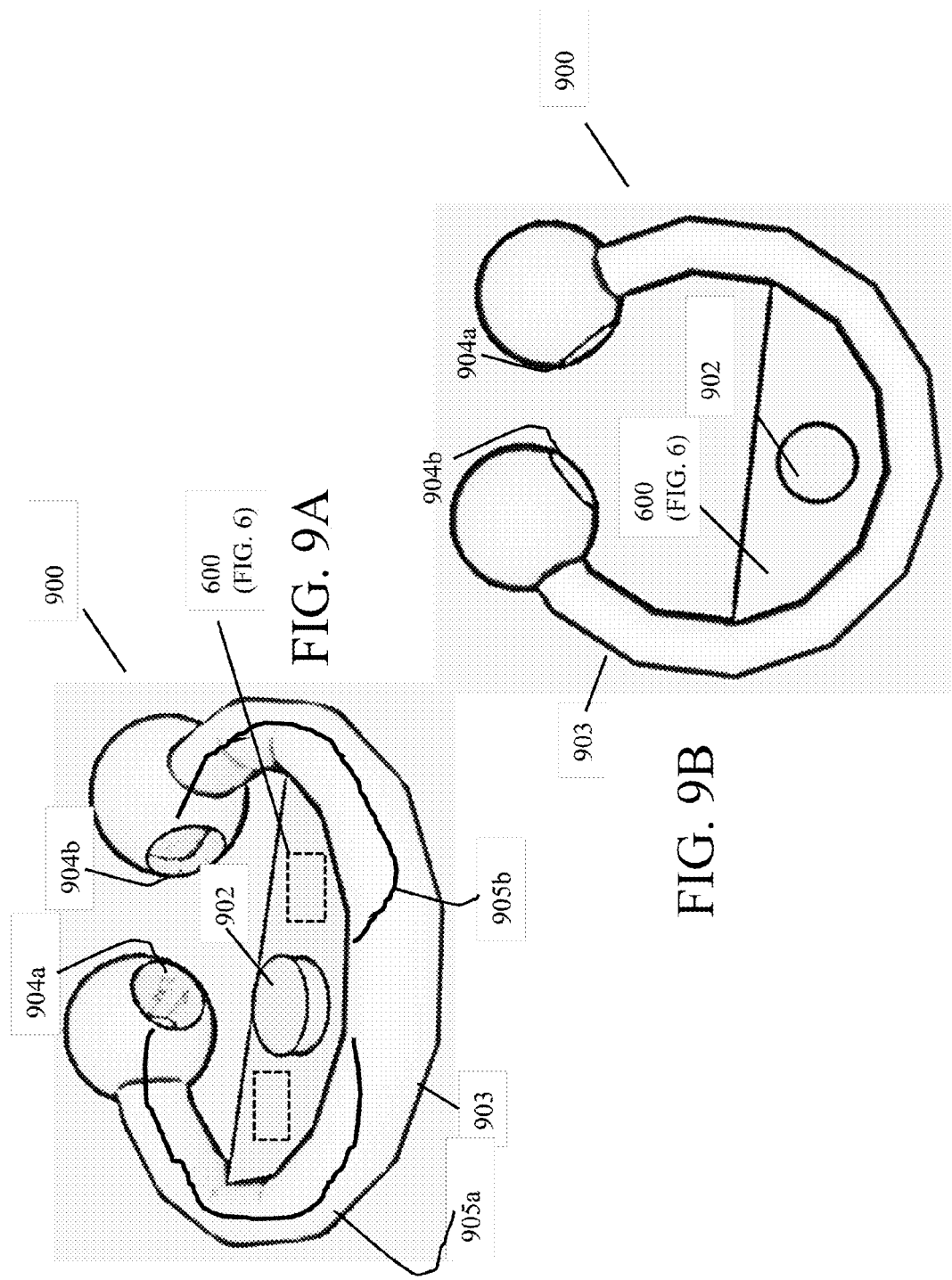

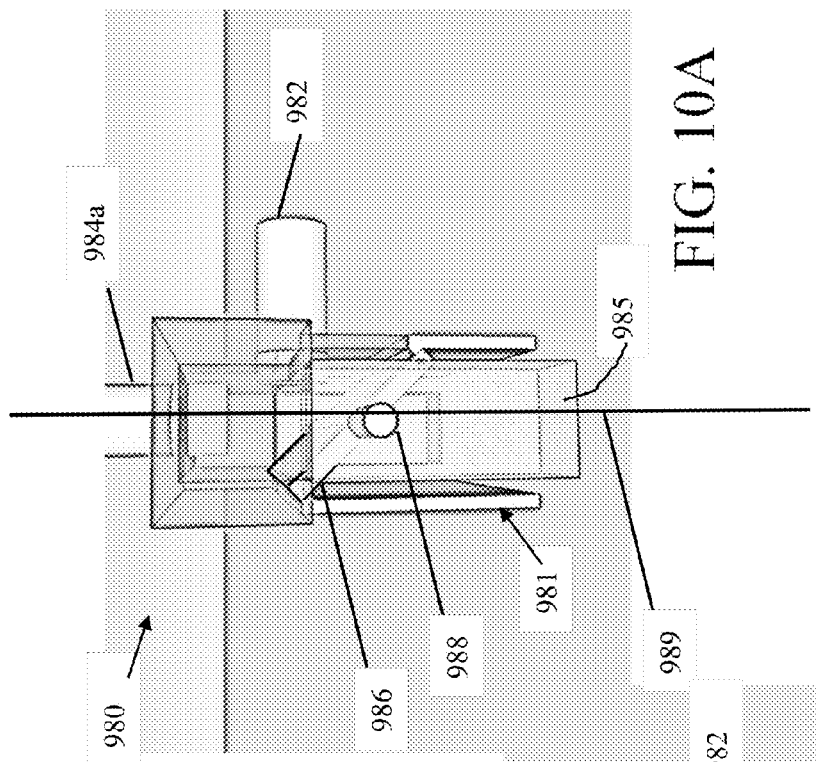
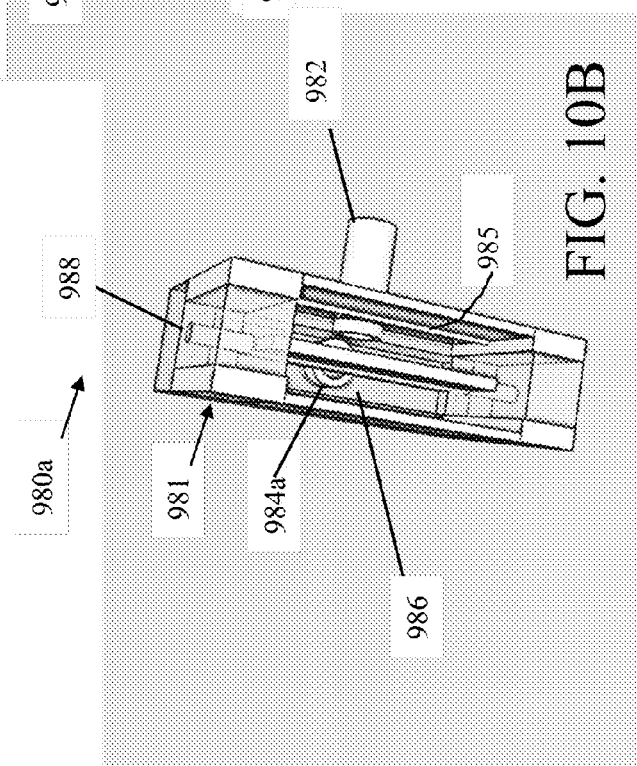

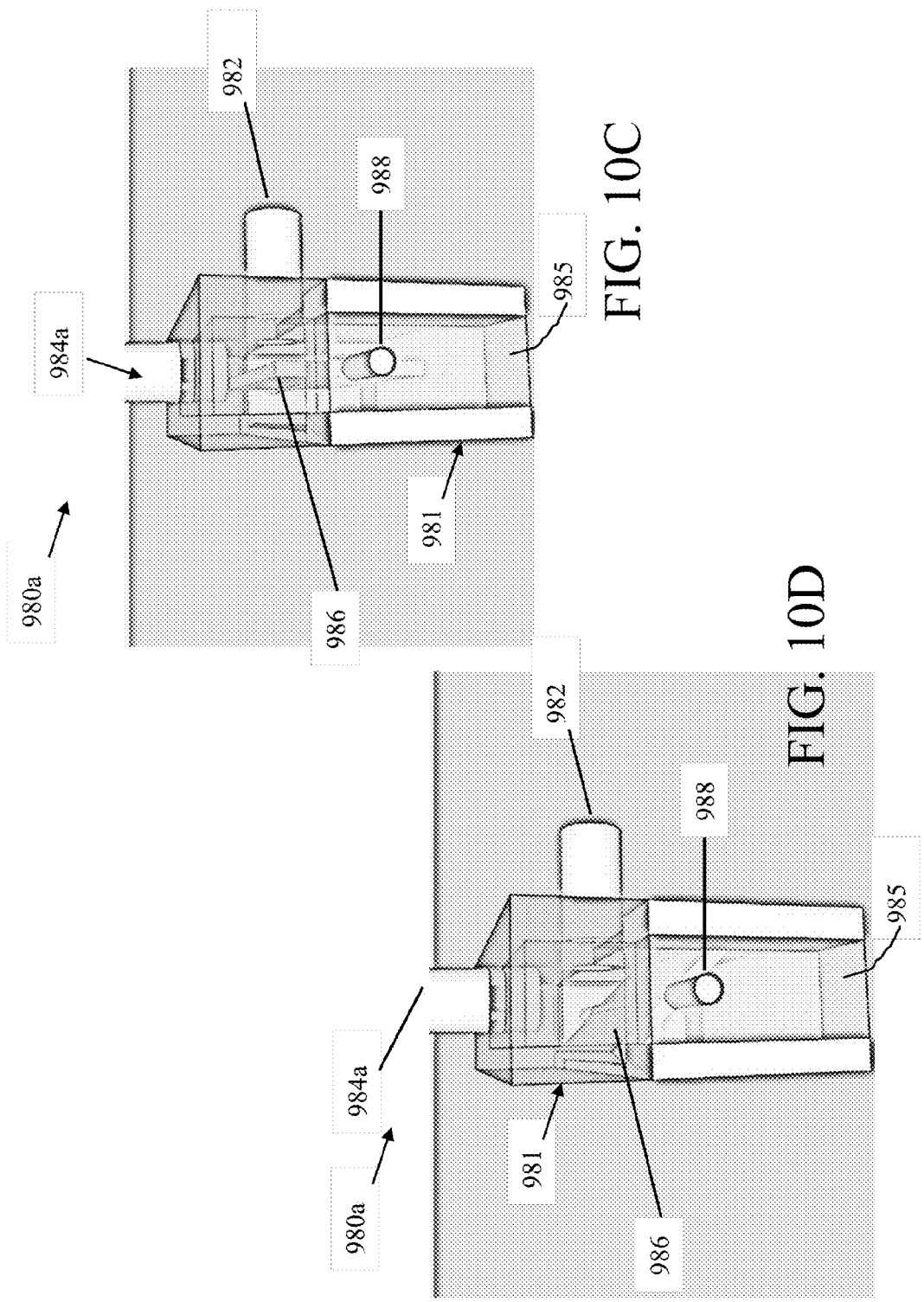

MICRO PUMP SYSTEMS

This application claims priority under 35 U.S.C. § 119 to U.S. Provisional Patent Application Ser. No. 61/945,973, filed Feb. 28, 2014, and entitled "Micro Pump Systems", the entire contents of which are hereby incorporated by reference.

BACKGROUND

This specification relates to pump systems.

Mechanical pump systems and compressor systems are well-known. Pump are used to move fluid (such as liquids or gases or slurries by mechanical action. Pumps can be classified according to the method used to move the fluid, e.g., a direct lift pump, a displacement pump, and a gravity pump.

Recently was announced a low-profile high pressure air pump operating with piezoelectric technology, by Murata Manufacturing, model MZB1001, micro-blower, a miniature piezoelectric air pump. According to Murata, the pump uses a piezoelectric diaphragm, which vibrates up and down when a sine wave voltage is applied, the vibrations force air into the micro-blower and out through a nozzle on the top of the device.

A somewhat common medical disorder sleep apnea involves a reduction or pause in breathing (airflow) during sleep. Sleep apnea is common among adults and rare among children. Treatments for sleep apnea can include surgical procedures or nonsurgical treatments that can involve behavioral changes dental appliances and mouthpieces. One nonsurgical treatment involves CPAP (continuous positive airway pressure) devices.

Continuous positive airway pressure (CPAP) is a non-surgical treatment that uses a machine to supply air pressure to hold a user's airway open so that it does not collapse during sleep. A machine delivers air through a nasal or face-mask under pressure. The machine blows heated, humidified air through a tube to a mask that is worn snugly to prevent the leakage of air. Masks come in several forms including nasal pillows, nasal masks, and full-face masks. The CPAP machine is a little larger than a toaster. It is portable and can be taken on trips. However, existing CPAP treatments are not easy to use, as it is not easy to sleep with a mask that blows air into the nose.

SUMMARY

According to an aspect, a micro-pump includes a pump body, the pump body having a pump chamber that is compartmentalized into plural compartments, with the pump chamber having a first plurality of inlet ports providing fluid ingress into the pump chamber and a second plurality of outlet ports providing fluid egress from the pump chamber, a third plurality of membranes disposed in the pump chamber, with the third plurality of membranes anchored between opposing walls of the pump body and providing the plural compartments with the pump chamber, and a fourth plurality of electrodes, with a first pair of the fourth plurality of electrodes disposed on a second different pair of opposing walls of the pump body, and a remaining ones of the fourth plurality of electrodes disposed on major surfaces of the membranes.

The follow are some embodiments within the scope of this aspect.

Inlets and outlets are on the same wall of the pump body. The first plurality of inlets and the second plurality of outlets are on the same wall of the pump body, and the first plurality of inlets have a first set of connections to a source and the second plurality of outlets have a second, different set of connections to a sink and with the second plurality of outlets isolated from the first set of connections. The inlets and the outlets are on opposing walls of the pump body. The micro-pump includes a fifth plurality of valves, a first portion of which are disposed adjacent the first plurality of inlets and a second portion of the valves disposed adjacent the second plurality of outlets. The fifth plurality of valves are flap valves. The micro-pump is configured to be driven by a set of electrical signals applied to the fourth plurality of electrodes to cause the third plurality of membranes disposed in the pump chamber to deflect according to polarities of voltages applied to the fourth plurality of electrodes. The set of electrical signals cause a first one of the plural compartments to compress and cause at least one adjacent one of the plural compartments to expand substantially simultaneously. The micro-pump includes a drive circuit to produce waveforms to apply to the electrodes.

According to an additional aspect, a micro-pump includes first and second micro-pump modules having a pump body, a membrane having electrically conductive electrodes on major surfaces thereof, and a pump end that form a pump compartment, each of the first and second micro-pump modules having at least an inlet port providing fluid ingress into the pump compartment and an outlet port providing fluid egress from the pump compartment, at least a third micro-pump module having a pump body and a membrane having electrically conductive electrodes on major surfaces thereof, with the third micro-pump module sandwiched between the first and second micro-pump modules.

The follow are some embodiments within the scope of this aspect.

The inlet and the outlet of each module are on a same wall of the pump body. The first plurality of inlets and the second plurality of outlets are on the same wall of the pump body, and the first plurality of inlets have a first set of connections to a source and the second plurality of outlets have a second, different set of connections to a sink and with the second plurality of outlets isolated from the first set of connections. The inlet and the outlet of each module are on opposing walls of the pump body. The micro-pump includes a plurality of valves disposed adjacent inlets and outlets. The valves are flap valves having a beam member and a stop.

According to an additional aspect, a cooling device for an electrical component, include a micro-pump having a pump body forming a pump chamber having a plurality of compartments, with the pump chamber having a first plurality of inlet ports providing fluid ingress into compartments of the pump chamber and a second plurality of outlet ports providing fluid egress from compartments of the pump chamber and a third plurality of membranes disposed in the pump chamber, with the third plurality of membranes anchored between opposing walls of the pump body, and a fourth plurality of electrodes, with a first pair of the fourth plurality of electrodes disposed on a second different pair of opposing walls of the pump body, and a remaining portion of the fourth plurality of electrodes disposed on a surface of each of the membranes, a heat plate having a first surface configured to attach to the electrical component and a second surface that is in thermal communication with the micro-pump.

The follow are some embodiments within the scope of this aspect.

The micro-pump is connected to the heat plate. End ones of the compartments have a corresponding wall of the pump body and one of the third plurality of membranes providing the end compartments and with intermediate ones of the compartments having a pair of membranes providing the intermediate compartments.

According to an additional aspect, an airway pressure breathing device includes a ring body having air passages through the ring body, terminating in a pair of end portions, with each end portion having at least one outlet in a first surface of the end portion, and a micro pump supported by the ring body, the micro pump configured to pump ambient air through the air passages in the ring body to the end portions.

The follow are some embodiments within the scope of this aspect.

The airway pressure breathing device includes a battery to provide a power source for the micro pump, the battery supported on the pump body.

One or more of the above aspects may provide one or more of the following advantages.

Micro pumps can be made using micro fabrication methods and can be used for performing micro pumping processes that are widely implemented in industrial, medical, and biological applications. The micro pumps can transport the fluids at high flow rates. The micro pumps can be used as reasonably inexpensive and possibly disposable apparatus for various applications, including to dose medications, can be used in artificial organs. The micro pumps can be used as vacuum pumps based on their high compression capabilities and can be used in heat transfer applications such as in fuel cell systems, replacing traditional air compressors to move air to provide oxygen for fuel cell reactions and remove reaction byproducts including water vapor and waste heat. Compared to the traditional air compressors, which can be expensive, loud, big, heavy, consumes high power, and easy to wear out, the micro pumps are low cost, quiet, small, e.g., in the millimeter scale, light weight, e.g., in the scale of milligram to gram, and generally will consume relatively low power in comparison to conventional pumps. Moreover, the micro pumps are mechanically robust.

The details of one or more embodiments of the invention are set forth in the accompanying drawings and the description below. Other features, objects, and advantages of the invention are apparent from the description and drawings, and from the claims.

DESCRIPTION OF DRAWINGS

FIGS. 9A and 9B are respective perspective view and front view of an airway pressure breathing device.

FIGS. 10A-10F are views of an exhalation valve.

DETAILED DESCRIPTION

Overview

Figure 1A:
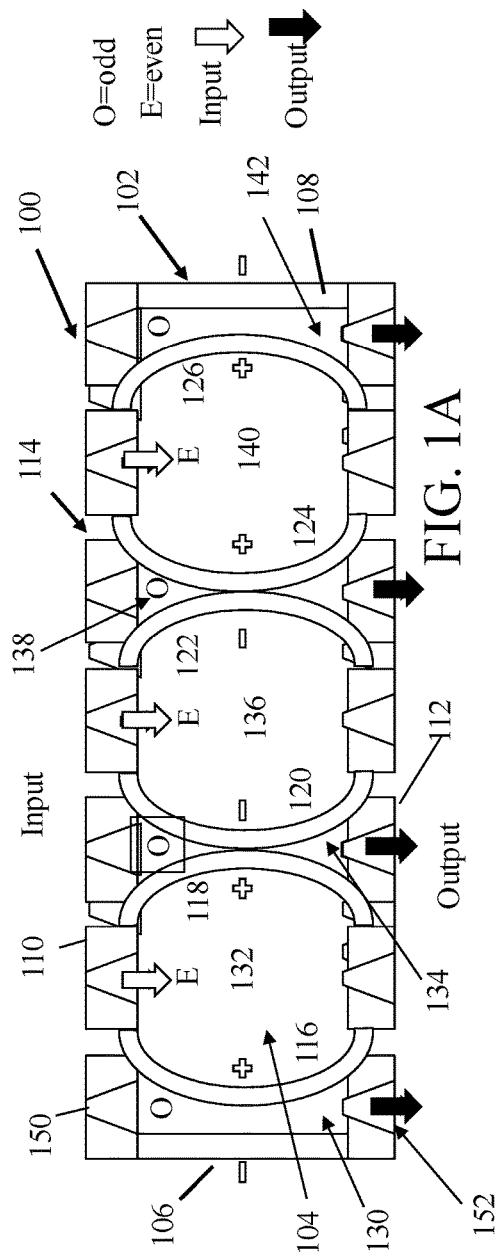
FIGS. 1A and 1B are functional block diagrams of a micro pump operating in two opposite phases of a pumping cycle.

Micro pumps can be made using micro fabrication methods and can be used for performing micro pumping processes that are widely implemented in industrial, medical, and biological applications. For example, micro pumps can be incorporated in lab-on-a-chip systems, fuel cells, high flux electronic cooling systems, and biochemistry systems. The micro pumps can transport fluids, e.g., gas or liquids, in small, accurately measured quantities. In some implementations, the micro pumps can transport the fluids at high flow rates, e.g., about microliters per second to about a few milliliters per second, and/or high pressure, e.g., about thousandths of one psi to about tenths of one psi. The micro pumps can be designed such that the fluid transport, the flow rates, and/or the pressure are scalable.

In medical applications, the micro pumps can be used as reasonably inexpensive and possibly disposable means of chemical dosing. For example, the micro pumps can be implanted in a human body to dose medications, e.g., into blood streams, and treat chronic diseases. The micro pumps can also be used in artificial organs.

The micro pumps can be used as vacuum pumps based on their high compression capabilities. The micro pumps when used as vacuum pumps, i.e., micro vacuum pumps can be used in miniature systems for chemical and biological analyses. For example, the micro vacuum pumps can be used to produce and maintain a vacuum in an ionization chamber of a mass spectrometer, so that ions produced in the ionization chamber exit the chamber without colliding with air molecules.

In fuel cell systems, the micro pumps can be used as air pumps, replacing traditional air compressors, to move air in the systems to provide oxygen for fuel cell reactions and remove reaction byproducts including water vapor and waste heat. Compared to the traditional air compressors, which can be expensive, loud, big, heavy, consumes high power, and easy to wear out, the micro pumps are low cost, quiet, small, e.g., in the millimeter scale, light weight, e.g., in the scale of milligram to gram, and generally will consume relatively low power in comparison to conventional pumps. Moreover, the micro pumps are mechanically robust.

In one example implementation, micro fuel cells are formed to include a small, light-weight and highly distributed air subsystem. The air subsystem incorporates micro pumps with three dimensional (3D) proton exchange membrane (PEM) structures on silicon wafers. Fabricated on the micron scale, the micro fuel cell architecture simplifies the air movement requirements for fuel cell reactions and for removing reaction by products. Compared to traditional fuel cells, fuel cells formed on silicon wafers can achieve improvement in power per volume production and weight per volume by an order of magnitude.

Micro Pump Systems

Micro Pumps

Referring to FIGS. 1A-1D, a micro pump 100 is shown to include a single compartmentalized pump chamber 104. The pump body 102 includes two walls 110, 112 along the pumping direction 114, and two fixed end walls 106, 108 opposite to each other along a direction perpendicular to the pumping direction 114. The walls 106, 108, 110 and 112 define the single chamber 104 that is compartmentalized by membranes. That is, between the two end walls 106, 108, membranes 116, 118, 120, 122, 124, 126 extend from the wall 110 to the wall 112, separating the pump chamber 104 into seven compartments 130, 132, 134, 136, 138, 140, 142. In this implementation, each compartment includes an inlet and an outlet defined in the walls 110, 112, respectively. For example, the compartment 130 includes an inlet 150 in the wall 110 and an outlet 152 in the wall 112. Other inlets and outlets are not labeled.

The compartments 130-142 are fluidically sealed from each other. In some implementations, different compartments can have the same inlet and/or the same outlet (not shown in the figure) and these different compartments may fluidically communicate with each other. Two compartments 130, 142 at the opposite ends of the pump chamber 104 have walls provided by a fixed wall of the pump body 102 and a membrane. Intermediate compartments between the compartments 130, 142 have walls provided by two membranes with the micro pump 100 having at least one and generally many intermediate compartments, each of which intermediate compartment walls are provided by two membranes. The micro pump 100 can pump fluids, e.g., gas or liquid, with selection of materials taking into consideration the type of fluid that the pump will be configured to pump.

Although six membranes are shown in the figures, the pump chamber can be extended with additional intermediate compartments, as each compartment can be viewed as formed of a module layer (see, FIGS. 2A-2D), and the pump 100 is formed of a stack of the module layers, as described further below.

Figure 1B:
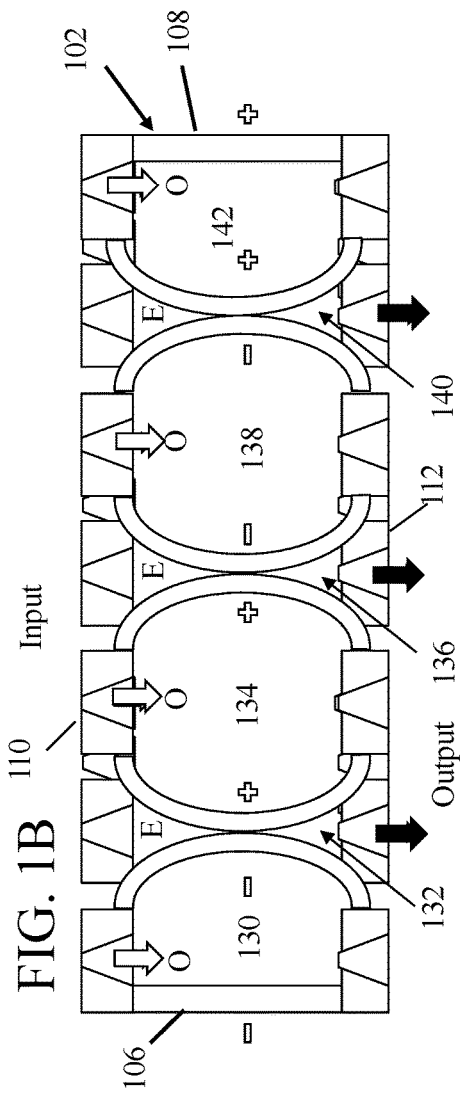

Electrodes (not explicitly shown in FIGS. 1A and 1B, see, FIGS. 2A and 2C) is attached to each of the membranes 116-126 and optionally to the end walls caps 106, 108. The electrodes (not explicitly shown) are connected to a drive circuit (see FIGS. 3-5) that delivers voltages to the electrodes to activate the membranes through electrostatic attraction/repulsion. When the electrodes have no voltage the membranes are not active and the membranes rest at nominal positions. Each membrane at rest can be substantially parallel to the end walls 106, 108 and the compartments 132-140 can have the same nominal volume $V_i$. When activated, the electrodes receive a voltage potential as shown in FIG. 1A and FIG. 1B. FIG. 1A and FIG. 1B show the same chamber but with different phases of signals applied to the electrodes, as discussed below. For clarity the reference nos. in FIG. 1A, in general, are not repeated for FIG. 1B.

In some embodiments, the distance between two adjacent membranes in their nominal positions is about 50 microns and the nominal volume V can range from nanoliters to microliters to milliliters, e.g., 0.1 microliters. In some implementations, the compartments 130, 142 each has a nominal volume $V_e$ that is half the nominal volume of the intermediate compartments 132-140. For example, the distance between the membrane 116 in its nominal position and the end wall 106 or between the membrane 126 in its nominal position and the end wall 108 is about 25 microns. The nominal volume $V_e$ can range from nanoliters to microliters to milliliters, e.g., 0.05 microliters. The compartments 130-142 can also have different sizes. The sizes can be chosen based on, e.g., manufacturing, power consumption, and application considerations. For example, the compartments 130, 142 having a width of 25 microns can allow a start-up function with a reduced peak drive voltage. Drive voltages are discussed further below. As an example, the micro pump 100 can have an internal volume having a length of about 1.5 mm, a width of about 1.5 mm, a total height (the cumulative height of different compartments) of 0.05 mm, and a total volume of about 0.1125 mm$^3$.

Compared to a conventional mechanical pump used for similar purposes, the micro pump 100 uses less material, and thus is subject to less stress, and is driven using less power. The micro pump 100 has a size in the micron to millimeter scale, and can provide wide ranges of flow rates and pressure. Approximately, a potential flow rate that could be provided by micro pump 100 can be calculated as the total volume of the micro pump 100 times the drive frequency.

Generally, the flow rate can be in the scale of nanoliters to microliters to milliliters. Generally, the pressure is affected by how much energy, e.g., the drive voltage, is put into the micro pump 100. In some implementations, the higher the voltage, the larger the voltage, and the upper limit on voltage is defined by break down limits of the micro pump 100 and the lower limit on the voltage is defined by the membrane's ability to actuate. The pressure across a micro pump 100 can be in the range of about a micro psi to tenths of a psi. A selected range of flow rate and pressure can be accomplished by selection of pump materials, pump design, and pump manufacturing techniques.

The described micro pump 100 is a displacement type pump in the reciprocating category. Pumping occurs in two alternating operations of a fluid charging cycle and a fluid discharging cycle through the actuation of a pump chamber of the micro pump. In the charging operation, the pump chamber is opened to a lower pressure source and the fluid fills into the chamber. In the discharging operation, the fluid inside the pump chamber is compressed out of the pump chamber to a higher pressure sink.

Generally, while a conventional pump chamber is compressed when a single membrane moves towards a fixed wall of the chamber, the pump chamber discussed above in conjunction with FIGS. 1A, 1B comprises multiple membranes each anchored between two fixed walls. The fixed walls are pump body layers that form multiple compartments separated by pairs of adjacent membranes. The first and last ones of the compartments are formed by a membrane and a fixed wall that is part of an end cap of the body, but intermediate compartments are provided by pairs of adjacent membranes.

Comparing FIGS. 1A and 1B, which shows two operational states of the same micro pump 100. In a first half pump cycle a first set of compartments are compressed and a second set of compartments are expanded.

For instance in FIG. 1A, end compartments 130 and 142 are shown compressed as are intermediate compartments 134 and 138 in the first half pump cycle. The compression occurs in the end compartments 130 and 142 when membranes 116 and 126 move towards walls 106 and 108 and for compartments 134 and 138 when adjacent membranes 118, 120 and 122, 124 move towards each other. The movement of these membranes reduces the volume of the respective end compartments 130 and 142 and intermediate compartments 134 and 138 to discharge fluid (gas or liquid) from the compartments. Simultaneous to the compression of those compartments, adjacent compartments 132, 136 and 140 (all here being intermediate compartments) are charged when respective sets of membranes 116, 118; 120, 122; and 124, 126 move away from each other to expand the respective chamber volumes.

As shown in FIG. 1B, in a second half pump cycle, end compartments 130 and 142 are shown expanded as are intermediate compartments 134 and 138. The expansion occurs in the end compartments 130 and 142 when membranes 116 and 126 move away from walls 106 and 108 and for compartments 134 and 138 when adjacent membranes 118, 120 and 122, 124 move away from each other. The movement of these membranes increases the volume of the respective end compartments 130 and 142 and intermediate compartments 134 and 138 to charge fluid (gas or liquid) into those compartments. Simultaneous to the expansion of those compartments, adjacent compartments 132, 136 and 140 (all here being intermediate compartments) are discharged when respective sets of membranes 116, 118; 120, 122; and 124, 126 move towards each other to reduce the respective chamber volumes.

That is, when actuated, each membrane of a pump chamber can move in two opposite directions about a central, nominal location at which the membrane rests when it is not actuated.

In operation, the membrane of the conventional pump chamber forms a single pump chamber compartment, which is used in pumping. Fluid, e.g., gas is charged and discharged once during the charging and discharging operations of a pumping cycle, respectively. The gas outflows only during half of the cycle, and the gas inflows during the other half of the cycle.

In the instant micro pump 100, each compartment 130, 132, 134, 136, 138, 140, and 142 is used in pumping. Thus, as shown in FIG. 1A in a first half of a pump cycle fluid is pumped out of chambers 130, 134, 138, and 142, while gas enters chambers 132, 136, and 140 simultaneously. As shown in FIG. 1B, in the second half of a pump cycle the operation is reversed, with fluid pumped out of chambers 132, 136, and 140 while gas enters chambers 130, 134, 138, and 142, simultaneously.

Various implementations are possible. For example, two membranes between two fixed end walls form three compartments for pumping. The micro pump 100 can have a higher efficiency and can consume less energy than a conventional pump performing the same amount pumping, e.g., because the individual membranes travel less distance and therefore are driven less. The efficiency and energy saving can further increase with more than a single compartment between the two fixed end walls compartments. Thus, a micro-pump 100 can have from one to several to 100's or more intermediate chambers. Here in FIGS. 1A and 1B, five (5) intermediate chambers are shown.

Generally, to perform pumping, each compartment includes a gas inlet 150 and a gas outlet 152. The inlets and the outlets include valve, e.g., passive valves that open or close in response to pressure applied to the valves. In some implementations, the valves are flap valves that are driven by a differential pressure across the valves produced by flows of gas into or out of the pump compartments. Because no active driving is required, the flap valves can reduce the complication of pump operation.

In other implementations, the valves are sliding valves that are driven by differential pressure across the valves produced by flows of gas into or out of the pump compartments, and which may be more desirable given energy considerations involved with flexing the flap valve. Exemplary sliding valves are discussed in FIG. 11.

Alternatively, it is also possible to build micro pump 100 in a valve-less configuration using nozzles and diffusers.

Figure 1C:
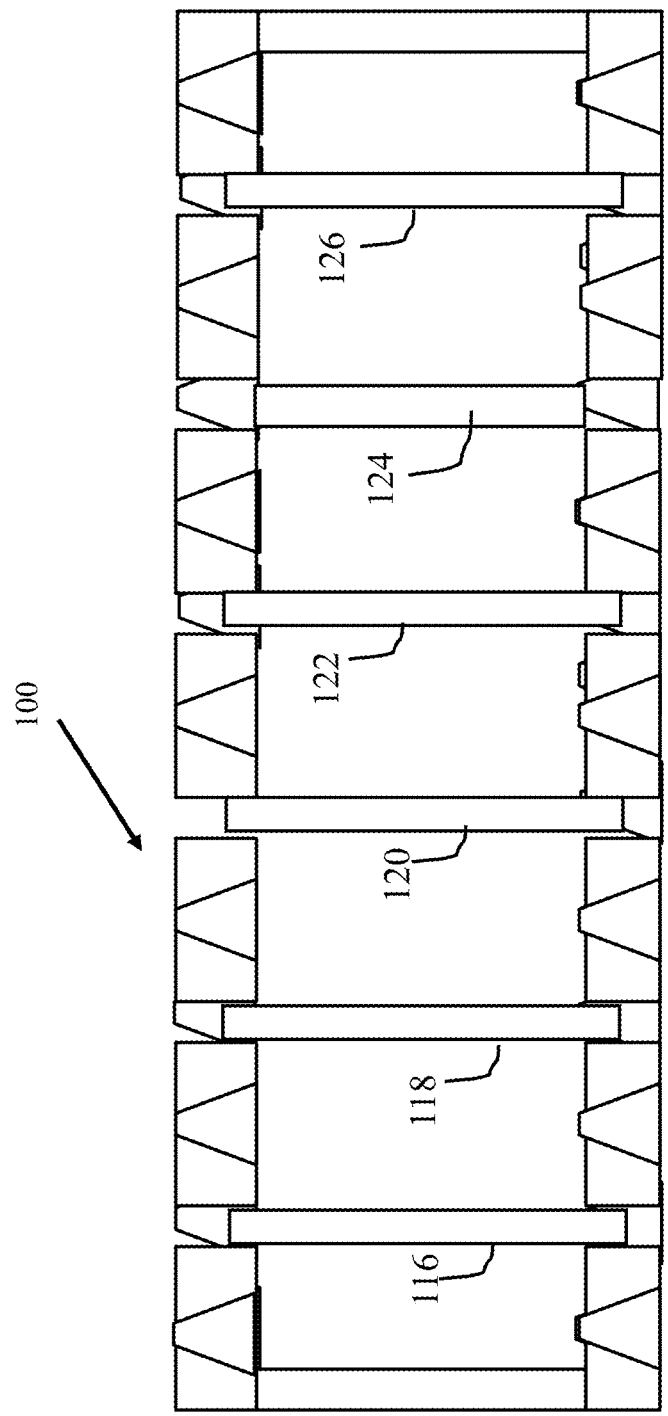
FIG. 1C illustrates the micro pump of FIGS. 1A, 1B with membranes in a nominal uncharged position.

FIG. 1C shows membranes of the micro pump 100 in their central, nominal position.

Figure 1D:
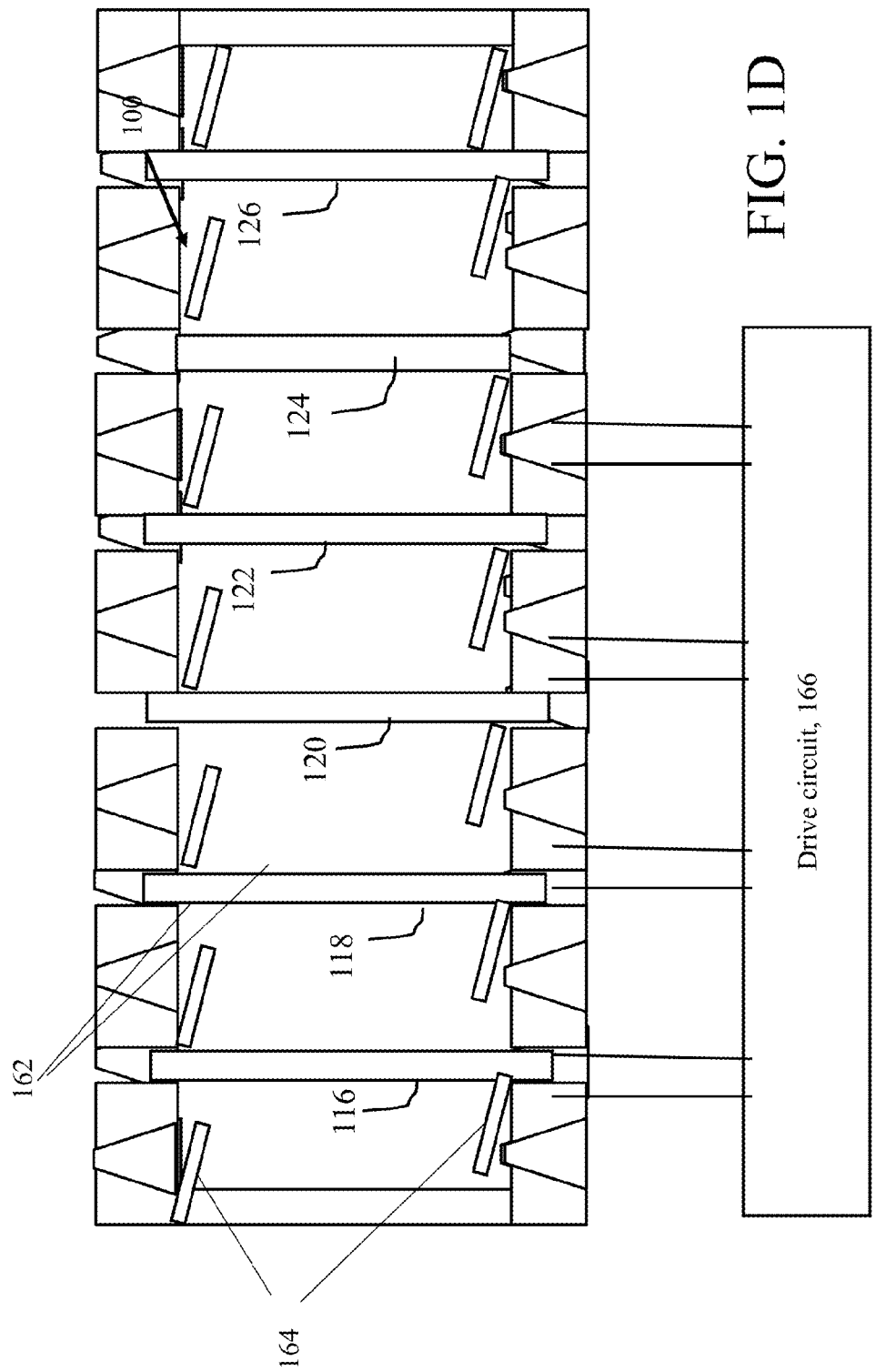
FIG. 1D illustrates the micro pump of FIGS. 1A, 1B with flap valves and drive circuitry.

Referring now to FIG. 1D, the membranes (not numbered but the same as in FIG. 1A) are driven to move by an electrostatic force. An electrode (generally 162) is attached to each of the major surfaces of each of the fixed end walls and membranes. During the charging operation of a compartment, adjacent electrodes of a compartment have the same positive or negative voltage applies and thus would tend to cause the two electrodes and therefore the two membranes to repel each other. During the discharging operation of a compartment, two adjacent electrodes of the compartment have the opposite positive or negative voltages, causing the two electrodes and therefore, the two membranes to attract to each other. The two electrodes of a compartment form a parallel plate electrostatic actuator. The electrodes generally have small sizes and low static power consumption. A high voltage can be applied to each electrode to actuate the compartment. But the actuation can be performed at a relatively low current.

Figure 1E:
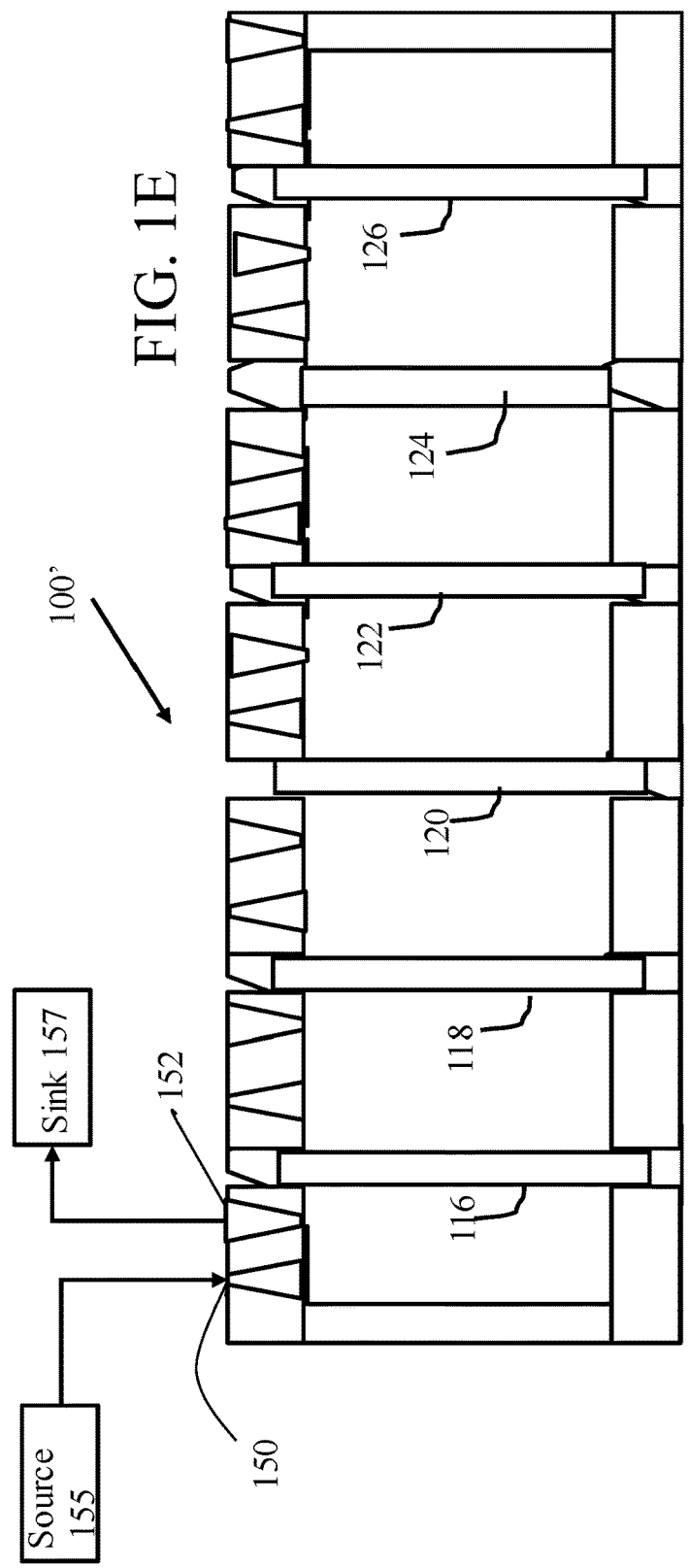
FIG. 1E illustrates the micro pump of FIGS. 1A, 1B with valves on the same wall and with a fluid source and a fluid sink.

Referring now to FIG. 1E, a micro pump 100' is shown having the inlets 150 and the outlets 152 being on the same wall (not referenced, but see FIGS. 1A, 1B). Connections (not referenced) of the inlets 150 and the outlets 152 are provided to a source 155 and a sink 157 of fluid, respectively. In FIG. 1E only one set of connections is shown and only one set of inlets and outlets are referenced. The set of connections are different. The outlets 152 are isolated from the set of connections to the inlets 150, etc.

As described previously, each membrane of the micro pump 100 moves in two opposite directions relative to its central, nominal position (illustrated for micro pump 100 in FIG. 1C). Accordingly, compared to a compartment in a conventional pump, to expand or reduce a compartment by the same amount of volume, the membrane of this specification travels a distance less than, e.g., half of, the membrane in the conventional pump. As a result, the membrane experiences less flexing and less stress, leading to longer life and allowing for greater choice of materials. In addition, because the travel distance of the membrane is relatively small, the starting drive voltage for the electrode on the membrane can be relatively low. Accordingly, less power is consumed. For a compartment having two membranes, since both membranes are moving, the time it takes to reach the pull-in voltage can be shorter.

Still referring to FIG. 1D, in some implementations, a drive circuit 166 for applying voltages to the electrodes takes a low DC voltage supply and converts it to an AC waveform. The frequency and shape of the waveform can be controlled by a voltage controlled oscillator. The drive voltage can be stepped up by a multiplier circuit to the required level. Flap valves 164 are also shown and are driven by differential pressure across the valves 164 produced by flows of gas into or out of the pump compartments.

Micro pumps 100 having the above described features can be manufactured using various methods such as MEMS processing techniques so-called roll to roll (R2R) processing. The materials for a micro pump 100 are chosen based on the features to be provided by the micro pump 100 and the method of manufacturing the micro pump. Below are some criteria for choosing the materials of the different parts of the micro pump.

Pump body and valves—The material used for the body of a pump may be defined by the requirements of the flap valves 164. Flap valves can be made of the same material as the body. In some implementations, the material needs to be strong or stiff enough to hold its shape to produce the pump chamber volume, yet elastic enough to allow the flap valves to move as desired. In addition, the choice can be influenced by the geometric design of the flap valves. In some implementations, the material is etchable or photo sensitive so that its features can be defined and machined/developed. Sometimes it is also desirable that the material interact well, e.g., adheres, with the other materials in the micro pump. Furthermore, the material is electrically non-conductive. Examples of suitable materials include SU8 (negative epoxy resist), and PMMA (Polymethyl methacrylate) resist.

Membrane—The material for this part forms a tympanic structure that is used to charge and discharge the pump chamber. As such, the material is required to bend or stretch back and forth over a desired distance and has elastic characteristics. In some implementations, the membrane material is impermeable to fluids, including gas and liquids, is electrically non-conductive, and possesses a high breakdown voltage. Examples of suitable materials include silicon nitride, and Teflon.

Electrodes—This material is electrically conductive. Because the electrodes do not conduct much current, the material can have a high electrical resistance, although the high resistance feature is not necessarily desirable. The electrodes are subject to bending and stretching with the membranes, and therefore, it is desirable that the material is supple to handle the bending and stretching without fatigue and failure. In addition, the electrode material and the membrane material adhere well, e.g., do not delaminate from each other, under the conditions of operation. Examples of suitable materials include very thin layers of gold and platinum.

Electrical interconnects—The drive voltage is conducted to the electrode on each membrane of each compartment. Electrically conducting paths to these electrodes can be built using conductive materials, e.g., gold and platinum.

Other materials—when MEMS processing is used in manufacturing the micro pump, a sacrificial filling material, e.g., polyvinyl alcohol (PVA), can be used. The sacrificial filling material may also be used in R2R processing. In some implementations, solvents are used in the manufacturing process, which may place additional requirements on the various building materials of the micro pump. It may be possible to print some of the electrical circuit components into the membranes. Sometimes a release material can be used for creating valve movement.

In general while certain materials have been specified above, other materials having similar properties to those mentioned could be used.

In FIGS. 2A-2D, a modularized micro pump is shown.

Figure 2A:
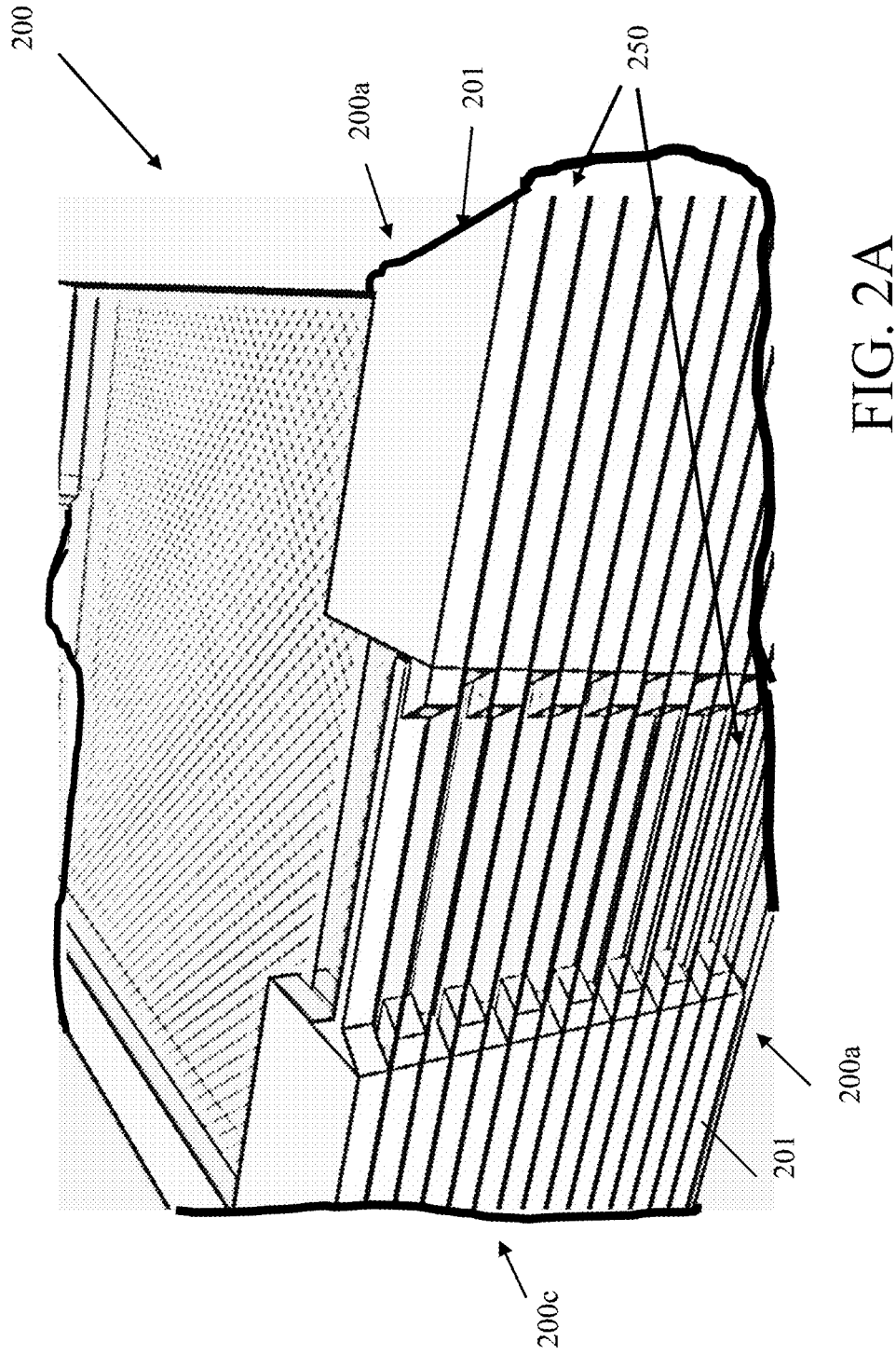
FIG. 2A is an assembled view of a stack of assembled module layers.

Referring to FIG. 2A a modularized micro pump 200 is comprised of module layers 201 (FIGS. 2B and 2C) to form end compartments 200a, 200b of the pump 200. The modularized micro pump 200 is also comprised of many module layers 250 (FIG. 2D) to form intermediate compartments 200c of the pump 200.

The valves in the micro pump 200 can be replaced by single valves connected to the input and the output or the individual valves in each layer can be staggered.

Figure 2B:
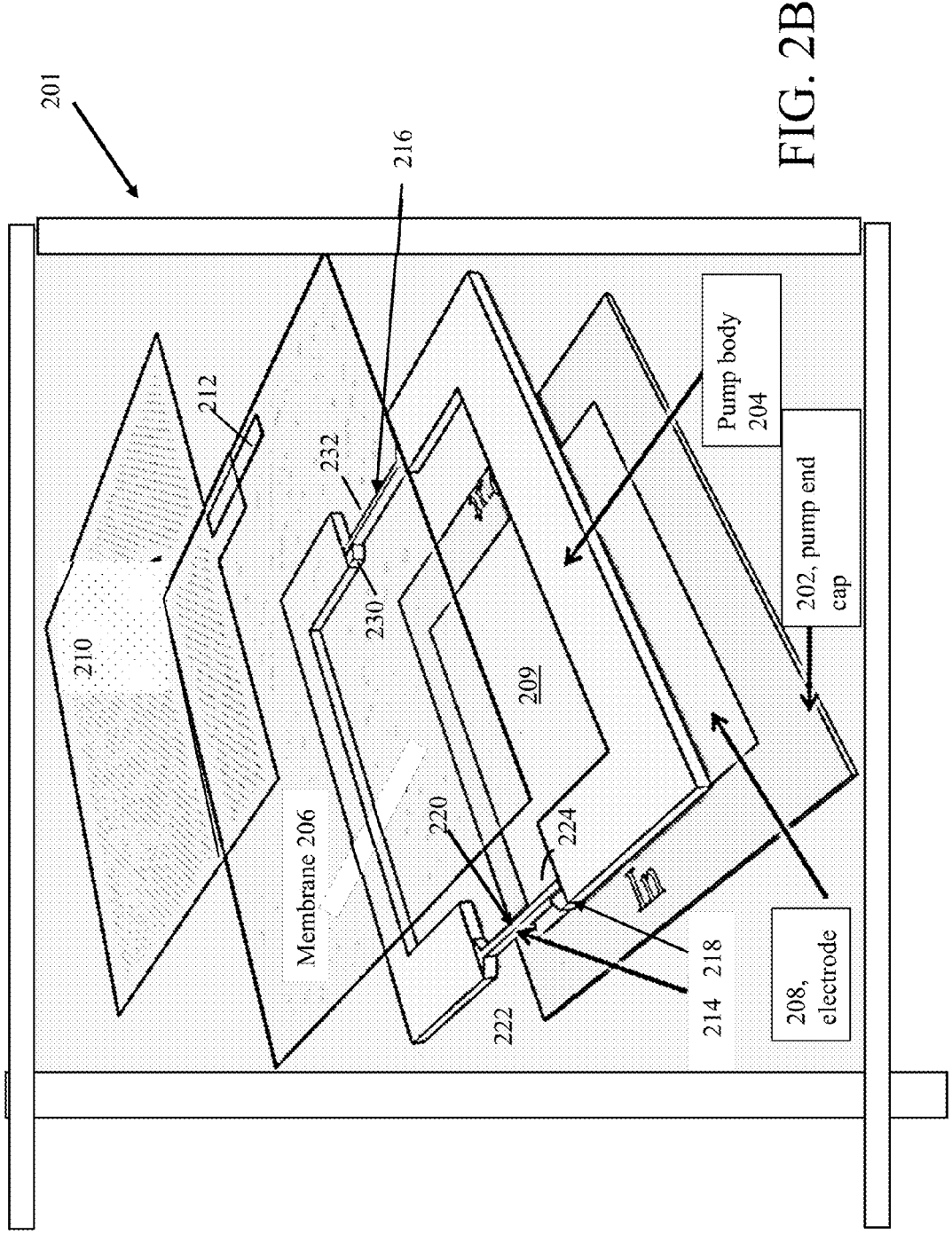
FIG. 2B is an exploded view of module layers.

Referring now to FIG. 2B, the module layers 201 each include a pump end cap 202 forming a fixed pump wall (similar to walls 106, 108 FIGS. 1A, 1B). An electrode 208 is attached to the pump end cap 202 for activating a compartment 209.

A single module layer 201 forms a portion of a pump body 204 between the pump end cap 202 with the electrode 208, and a membrane 206 along with an electrode 210 that is attached to the membrane 206 on the opposite side of the pump body 204 (similar as the membrane 116, 126 in FIGS. 1A, 1B). The electrode 210 includes a lead 212 to be connected to a drive circuit external to the module layer 200.

The membrane 206, the pump end cap 202, and the pump body 204 can have the same dimensions, and the electrodes 208, 210 can have smaller dimensions than the membrane 206 or the other elements. In some implementations, the membrane 206 has a dimension of about microns by microns to about millimeters by millimeters, and a thickness of about 5 microns. The pump body 204 has an outer dimension of about microns by microns to about millimeters by millimeters, a thickness of about 50 microns, and an inner dimension of about microns by microns to about millimeters by millimeters. The thickness of the pump body defines the nominal size of the compartment 209 (similar to compartments 130, 142 FIG. 1A). The electrodes 210, 202 have dimensions that substantially correspond to inner dimensions of the pump body 204. In some implementations, the electrodes have a surface area of about 2.25 mm$^2$ and a thickness of about 0.5 microns. An assembled module layer 201 is shown in FIG. 2C.

Figure 2C:
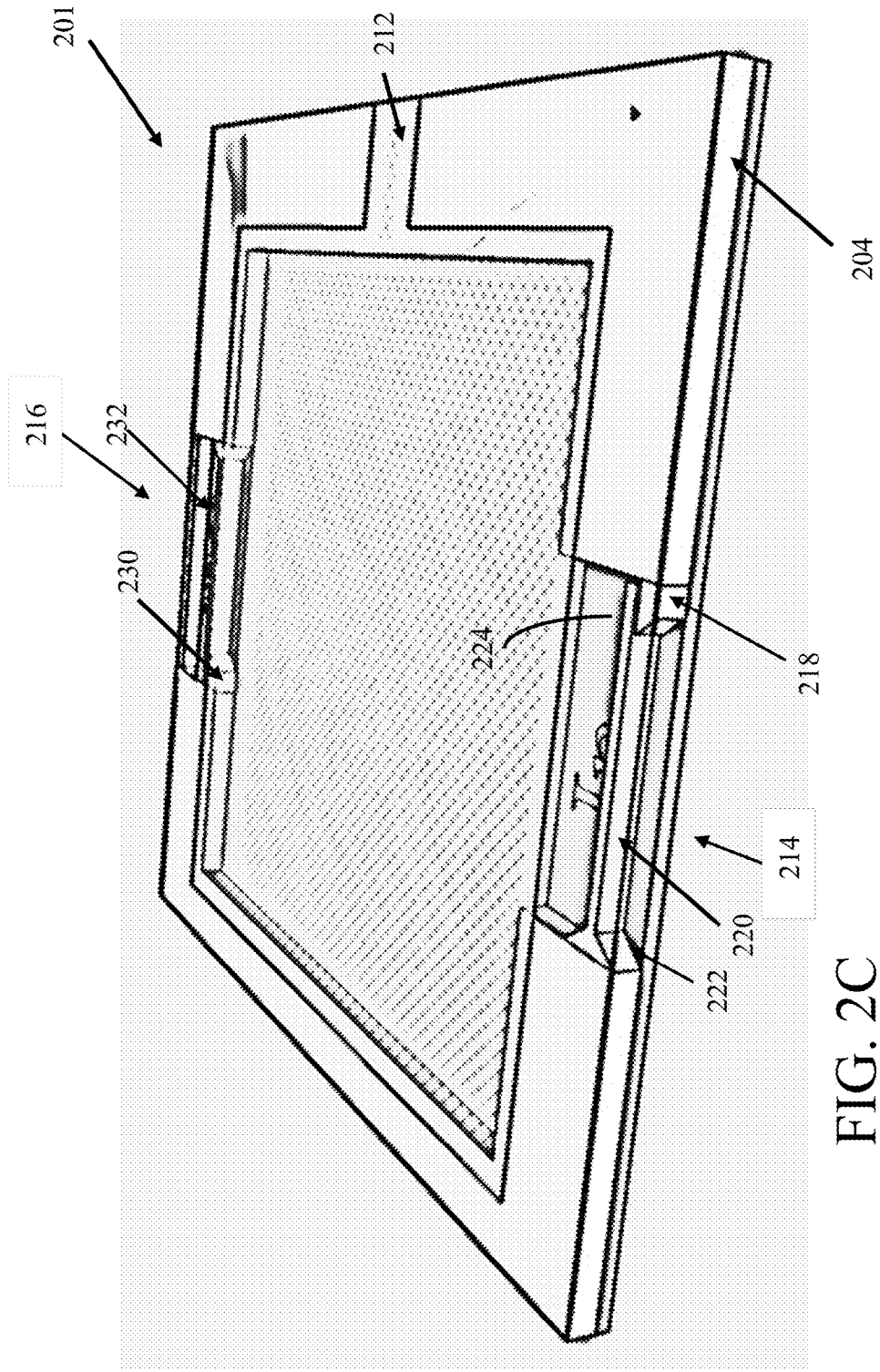
FIG. 2C is an assembled view of the module layer of FIG. 2B.

Referring now also to FIG. 2C, the pump body 204 includes two passive valves 214, 216, (flap valves) forming an inlet and an outlet, respectively. The inlet valve 214 includes a stopper (i.e., a stop) 218 and a flap 220 (i.e., a beam). The stopper or stop is connected to the pump body 204 and is located external to the compartment 130, 140 formed by the pump body. The flap 220 or beam has one end 222 attached to the pump body 204 and another end 224 movable relative to the stopper 218 and the pump body 204. In particular, the end 224 of the flap can bend towards the interior of the compartment 130, 140 when a pressure differential is established such that the pressure external to the module layer is larger than the pressure inside the module layer. For example, such a pressure differential is established during a charging operation in which a fluid flows from outside the module layer into the compartment 209. When the internal pressure is higher than the external pressure, e.g., during a discharge operation in which a fluid flows from the compartment 209 away to the outside of the module layer, the flap 224 bends towards the stopper and is stopped by the stopper 218. Accordingly, during the discharge operation, the fluid in the compartment 209 does not flow out from the inlet valve 214.

The outlet valve 216 also includes a stopper 230 and a flap 232 similar to the stopper 218 and the flap 220, respectively. However, the stopper 230 is located in front of the flap 232 along a direction in which the fluid flows into or out of the compartment 209. When the internal pressure is higher than the external pressure, the flap bends away from the stopper to open the valve and when the internal pressure is lower than the external pressure, the flap bends towards from the stopper to close the valve. Effectively, during the charging operation, the outlet valve 216 is closed so that the fluid does not flow out of the valve 216, and during the discharging operation, the outlet valve 216 is open and the fluid flows out from the valve 216.

Figure 2D:
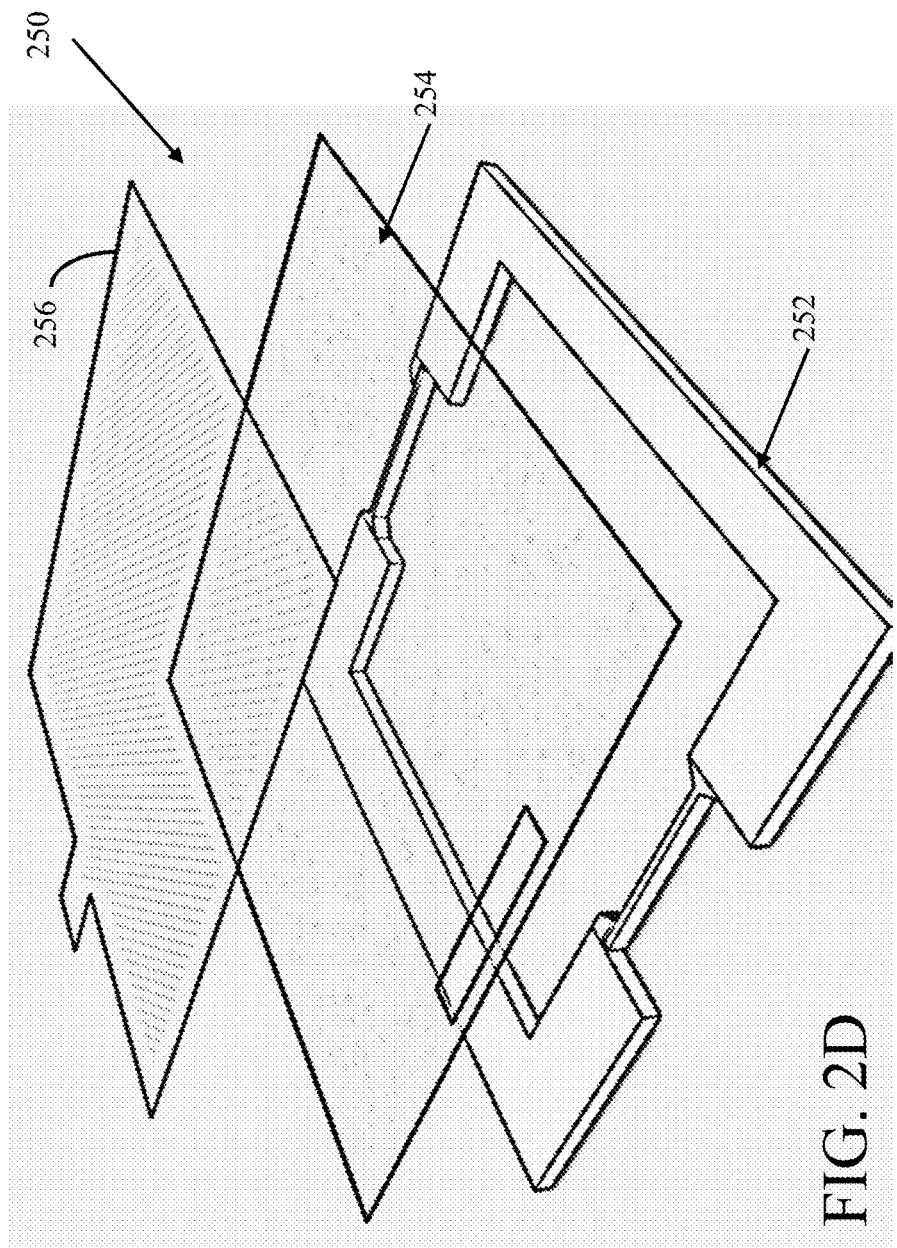
FIG. 2D is an exploded view of an intermediate module layer.

Referring to FIG. 2D, intermediate compartments (similar to compartments 132-140 FIGS. 1A-B) can each be formed using a module layer 250. The module layer 250 includes a pump body 252, an electrode 256, and a membrane 254 formed between the electrode 256 and the pump body 252. The pump body 252 can have similar or the same features as the pump body 204, the electrode 256 can have similar or the same features as the electrode 208, and the membrane 254 can have similar or the same features as the membrane 206. The module layer 250 also includes flap valves (not referenced but shown in the figure.)

As described previously, the valves of each pump body can be formed integrally with the pump body. Although the electrodes are shown as a pre-prepared sheet to be attached to the other elements, the electrodes can be formed directly onto those elements, e.g., by printing. The different elements of the module layers 200, 250 can be bonded to each other using an adhesive. In some implementations, a solvent can be used to partially melt the different elements and adhere them together.

Referring back to FIG. 2A, thus multiple, e.g., two, three, or any desired number of, module layers 250 of FIG. 2D are stacked on top of each other to form multiple intermediate compartments in a pump chamber. In the stack 200, each membrane is separated by a pump body and each pump body is separated by a membrane. To form a complete pump, a module layer 201 of FIG. 2B is placed on each of the top and bottom ends of the stack 200 so that the pump end caps of the module layer 201 form two fixed end walls of the pump chamber.

Referring again to FIGS. 1A and 1B, during each pumping cycle, the compartments are activated such that each compartment charges during half of the cycle and discharges during the other half of the cycle. Adjacent compartments operate in 180 degree phase difference, i.e., when the compartment 130 is charging, its adjacent compartment 132 is discharging, and vice versa. As a result, every other compartment operates in phase. In FIGS. 1A and 1B, the compartments are labeled by odd-numbered ("O") compartments and even-numbered ("E") compartments, the O compartments are in phase with each other, the E compartments are in phase with each other, and the O compartments are out of phase relative to the E compartments.

To operate compartments of the pump in their discharging state, voltages of opposite signs are applied to the electrodes on opposing walls of these compartments. For example, as shown in FIG. 1A, the voltage of the electrode on the fixed wall 106 is negative while the voltage of the electrode on the membrane 116 is positive, or the voltage of the electrode on the membrane 118 is positive while the voltage of the electrode on the membrane 120 is negative, etc. Simultaneously, the other compartments of the pump are operated in their charging state. Voltages of the same signs are applied to the electrodes on opposing walls of these other compartments. The voltages of opposite signs cause the two opposing walls of the compartments to attract each other and the voltages of the same signs cause the two opposing walls of the compartments to repel each other. The fixed walls 106, 108 do not move. However, the membranes 116-126 move towards a direction of the attraction force or a direction of the repelling force. As a result, in half of a pumping cycle, the compartments 130, 134, 138, 142 discharge and the other compartments simultaneously charge (FIG. 1A), and in the other half of the pumping cycle, the compartments 132, 136, 140 discharge and the other compartments simultaneously charge (FIG. 1B).

In some implementations, the material of the membranes and the voltages to be applied to the membranes and the end walls 106, 108 are chosen such that when activated, each membrane expands substantially half the distance d between the nominal positions of adjacent membranes. In the end compartments 130, 142 where the distance between the nominal position of the membrane and the fixed wall is d/2, the activated membrane reduces the volume of the compartment to close to zero (in a discharging operation) and expands the volume of the compartment to close to $2*V_e$. For the intermediate compartments, by moving each membrane by d/2, a volume of a compartment is expanded to close to $2*V_i$ in a charging operation and reduced to close to zero in a discharging operation. The micro pump 100 can operate at a high efficiency.

The period of the pumping cycle can be determined based on the frequency of the drive voltage signals. In some implementations, the frequency of the drive voltage signal is about Hz to about KHz, e.g., about 2 KHz. A flow rate or pressure generated by the pumping of the micro pump 100 can be affected by the volume of each compartment, the amount of displacement the membranes make upon activation, and the pumping cycle period. Various flow rates, including high flow rates, e.g., in the order of ml/s, and pressure, including high pressure, e.g., in the order of tenths of one psi, can be achieved by selecting the different parameters, e.g., the magnitude of the drive voltage. As an example, a micro pump can include a total of 15 module layers, including two layers 200 of FIG. 2B and 13 layers 250 of FIG. 2C. This example micro pump can be drive at a frequency of about 843 Hz and consumes power of about 0.62 mW, and provides a flow rate of about 1.56 ml/s at about 0.0652 psi.

In some implementations, four types of electrical signals are used to drive the membranes. The four types are:

V−: a DC reference for all the voltages; may be used to drive some membranes directly;

V+: a DC high voltage used to drive some membranes directly and switched for others;

V1: a periodic AC waveform used to drive some membranes to control operation. It includes a 50% duty cycle and swings between V− and V+ in one full pumping cycle.

V2: identical to V1 except it is 180 degrees out of phase.

Furthermore, based on the phenomenon of pull-in and drop-out voltages, the drive voltage can be reduced to a lower voltage once the highest magnitude of V1 or V2 has been reached. In particular:

V1.5: the pull-in voltage value.

V2.5: the drop-out voltage value.

Figure 3:
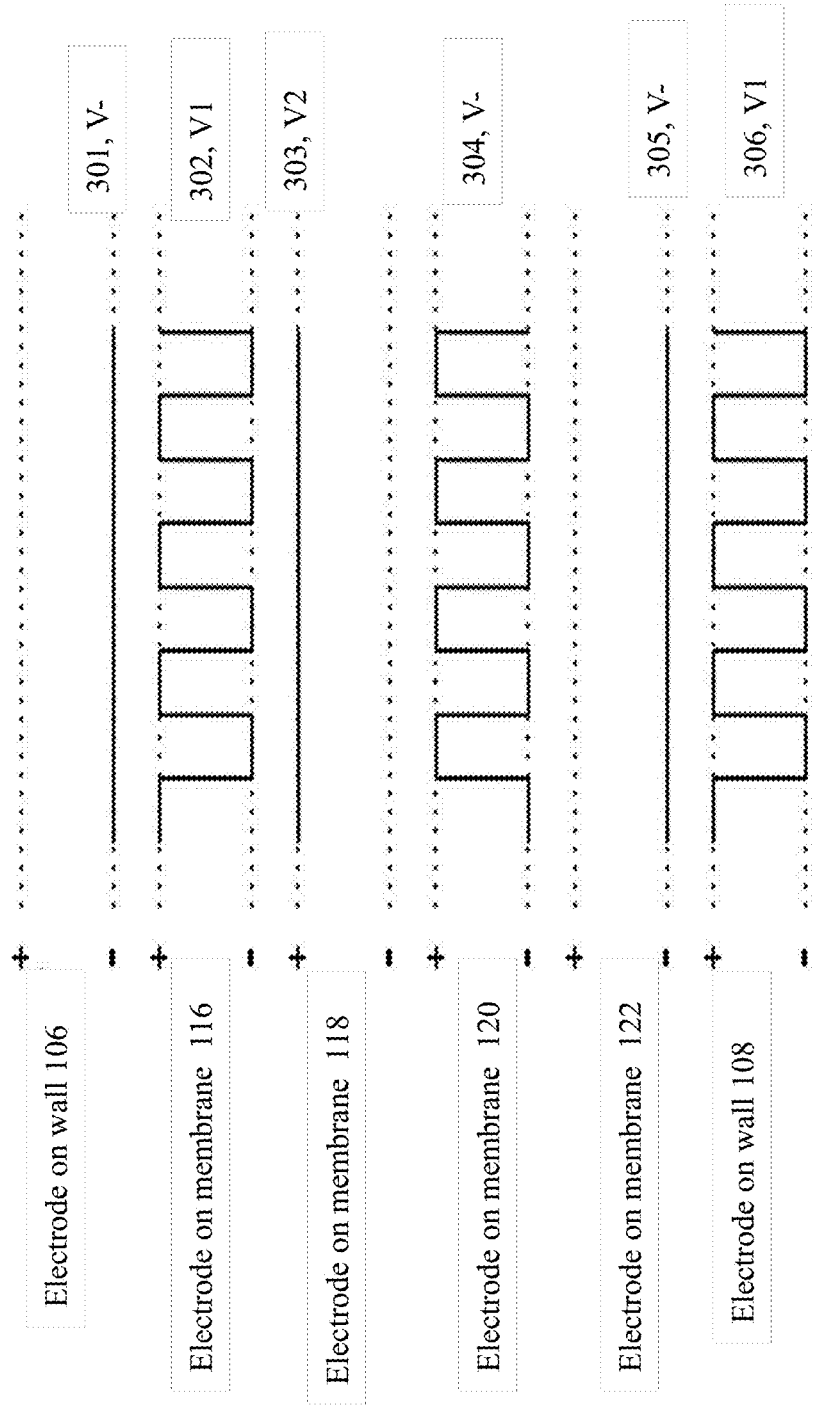
FIGS. 3 and 4 are plots of voltage waveforms for application to electrodes of a micro pump.

Referring now to FIG. 3, six example sets of waveforms 301-306 for application onto six electrodes on the fixed wall 106 and the membranes 116-124, respectively are shown. The waveforms applied to other additional membranes and fixed wall in the micro pump 100 or other micro pumps can be derived by the pattern shown in FIG. 3. During pumping cycles, V− of the first set of waveform 301 is constantly applied to the electrode on the fixed wall 106. The second set of waveform 302 for applying to the membrane 116 is in the form of V1. The third set of waveform 303 is V+ and is constantly applied to the membrane 118. The fourth set of waveform 304 is V2 for applying to the membrane 120. The fifth set of waveform 305 and sixth set of waveform 306 are a repeat of the first and second waveforms 301, 302. If additional waveforms are needed for other membranes, e.g., membranes 124 and 126 (FIG. 1A) the repetition continues with the third and fourth waveforms, and etc.

In some implementations, the magnitudes of V1, V2, V−, and V+ are the same. In other implementations, magnitudes of at least some of these voltages are different. Although a particular pattern of waveforms are shown, the electrodes of the pump 100 can also be activated by other patterns of waveforms.

Figure 4:
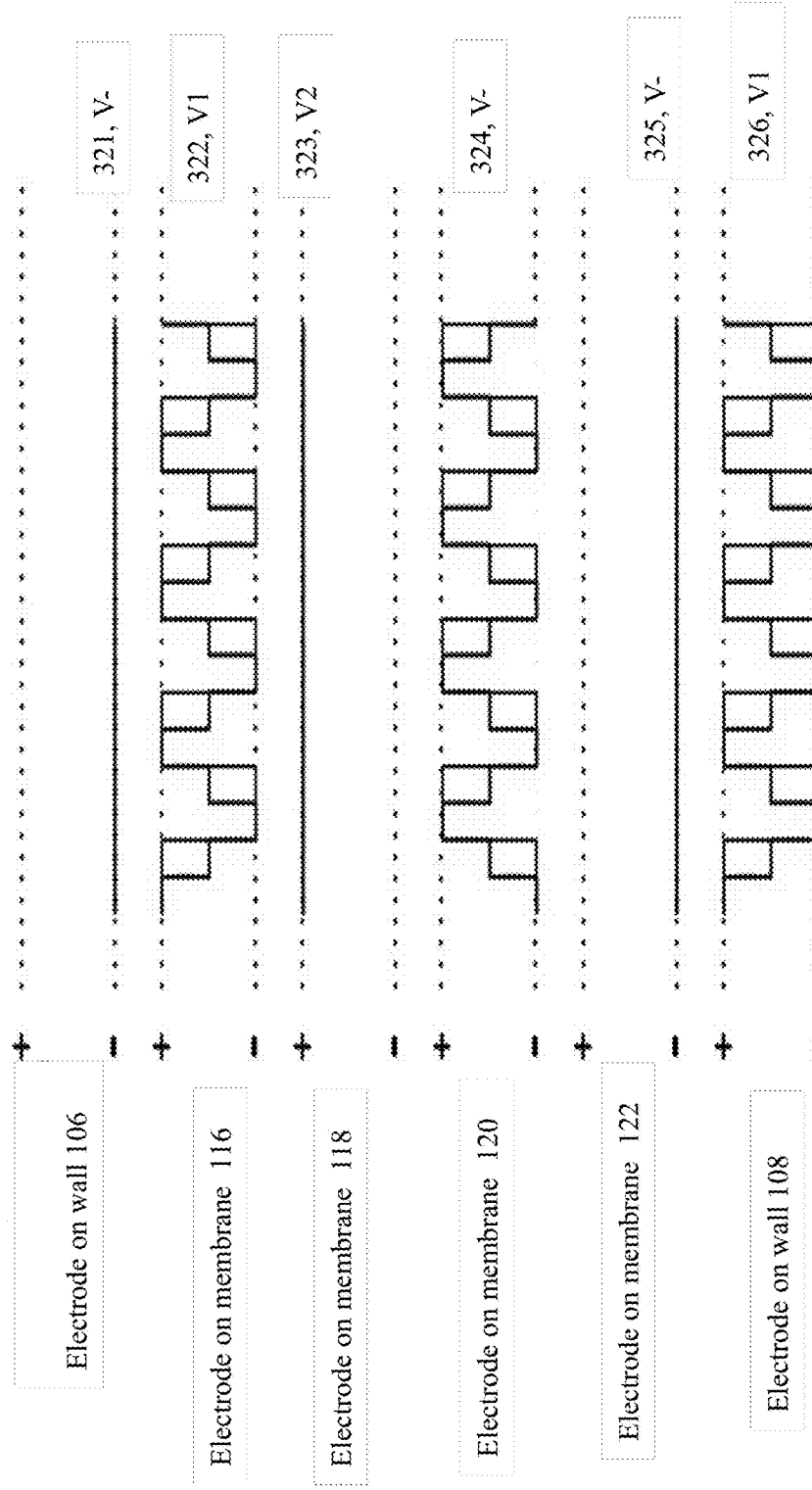

Referring now to FIG. 4, six sets of waveforms 321-326 corresponding to the six sets of waveforms 301-306 of FIG. 3, respectively are shown. The difference between the sets shown in FIG. 4 and the sets shown in FIG. 3 is that the AC voltage waveforms V1 and V2 of FIG. 3 are reshaped into V1.5 and V2.5, respectively to take the advantage of pull-in and drop-out phenomena.

In this example, in the waveform sets 322, 324, 326, the positive going voltage is stepped down (shown by arrows ↓) to a lower voltage once the pull-in point has been reached. This lower voltage is still greater than the drop-out voltage so that the membranes remain in their driven state. The next voltage transition defines the beginning of the opposite operation, during which a similar voltage level shift is applied. The negative going voltage is stepped up (shown by arrows ↑) to a voltage having a smaller magnitude. The power consumption of the pump 100 can be reduced by reducing the magnitude of the drive voltages during their hold time.

Drive Circuitry

Figure 5:
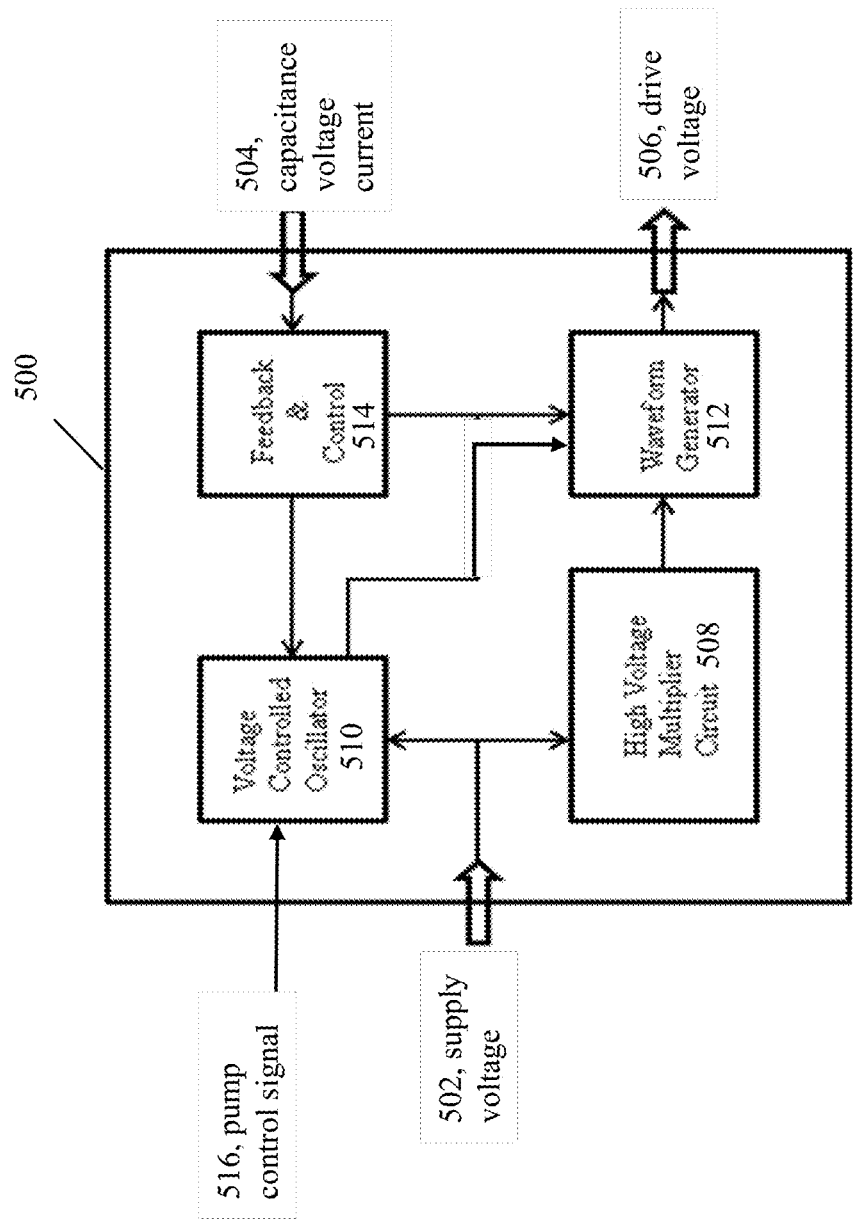
FIG. 5 is a block diagram of an exemplary drive circuit.

Referring now to FIG. 5, an example of drive circuitry 500 for applying voltages, such as those shown in FIG. 3 or FIG. 4 is shown. The drive circuitry 500 receives a supply voltage 502, a capacitance voltage current 504 signal, and pump control 516, and outputs drive voltages 506 to electrodes of a micro pump, such as the micro pump of FIGS. 1A and 1B. In some implementations, the supply voltage 502 is provided from a system in which the micro pump 100 is used. The supply voltage can also be provided by an isolation circuit (not shown).

The drive circuitry 500 includes a high voltage multiplier circuit 508, a voltage controlled oscillator ("VCO") 510, a waveform generator circuit 512, and a feedback and control circuit 514. The high voltage multiplier circuit 508 multiplies the supply voltage 502 up to a desired high voltage value, e.g., about 100V to 700V, nominally, 500 V. Other voltages depending on material characteristics, such as dielectric constants, thicknesses, mechanical modulus characteristics, electrode spacing, etc. can be used. In some implementations, the high voltage multiplier circuit 508 includes a voltage step-up circuit (not shown). The voltage controlled oscillator 510 produces a drive frequency for the micro pumps. The oscillator 510 is voltage controlled and the frequency can be changed by an external pump control signal 516 so that the pump 100 pushes more or less fluid based on flow rate requirements. The waveform generator circuit 512 generates the drive voltages for the electrodes. As described previously, some of the drive voltages are AC voltages with a specific phase relationship to each other. The waveform generator circuit 512 controls these phases as well as the shape of the waveforms. The feedback and control circuit 514 receives signals that provide measures of capacitance, voltage and or current in the micro pump and the circuit 514 can produce a feedback signal to provide additional control of the waveform generator 512 of the circuit 500 to help adjust the drive voltages for desired performance.

Integration of the Systems in Devices

The micro pump systems described above can be integrated in different products or devices to perform different functions. For example, the micro pump systems can replace a fan or a blower in a device, e.g., a computer or a refrigerator, as air movers to move air. Compared to the conventional fans or blowers, the micro pumps may be able to perform better at a lower cost with a higher reliability. In some implementations, these air movers are directly built into a host at a fundamental level in a massively parallel configuration.

In some implementations, the micro pump systems receive power from a host product into which the systems are integrated. The power can be received in the form of a single, relatively low voltage, e.g., as low as 5V or lower, to a drive circuitry of the micro pump systems, e.g., the drive circuitry 500 of FIG. 5.

System Configuration

The module layer stack of FIGS. 1A, 1B, and 2D can be viewed as module layers connected in parallel. The volume of each individual module layer, $V_i$ or $V_e$, is small. In some implementations, even the total volume of all layers in the stack is relatively small. In some implementations, multiple stacks or micro pumps can be connected in parallel to increase the total volume flow rate.

Similarly, the pressure capability of an individual micro pump is relatively low. Even though there are multiple module layers in a stack, the layers do not increase the total pressure of the stack because they are connected in parallel. However, the pressure of the stack can be increased when multiple stacks or micro pumps are connected in series. In some implementations, the pumps connected in series are driven at different speeds to compensate for different mass flow rates. For example, built-in plenums or plumbing in a tree type configuration can also be used to compensate for different mass flow rates.

Figure 6:
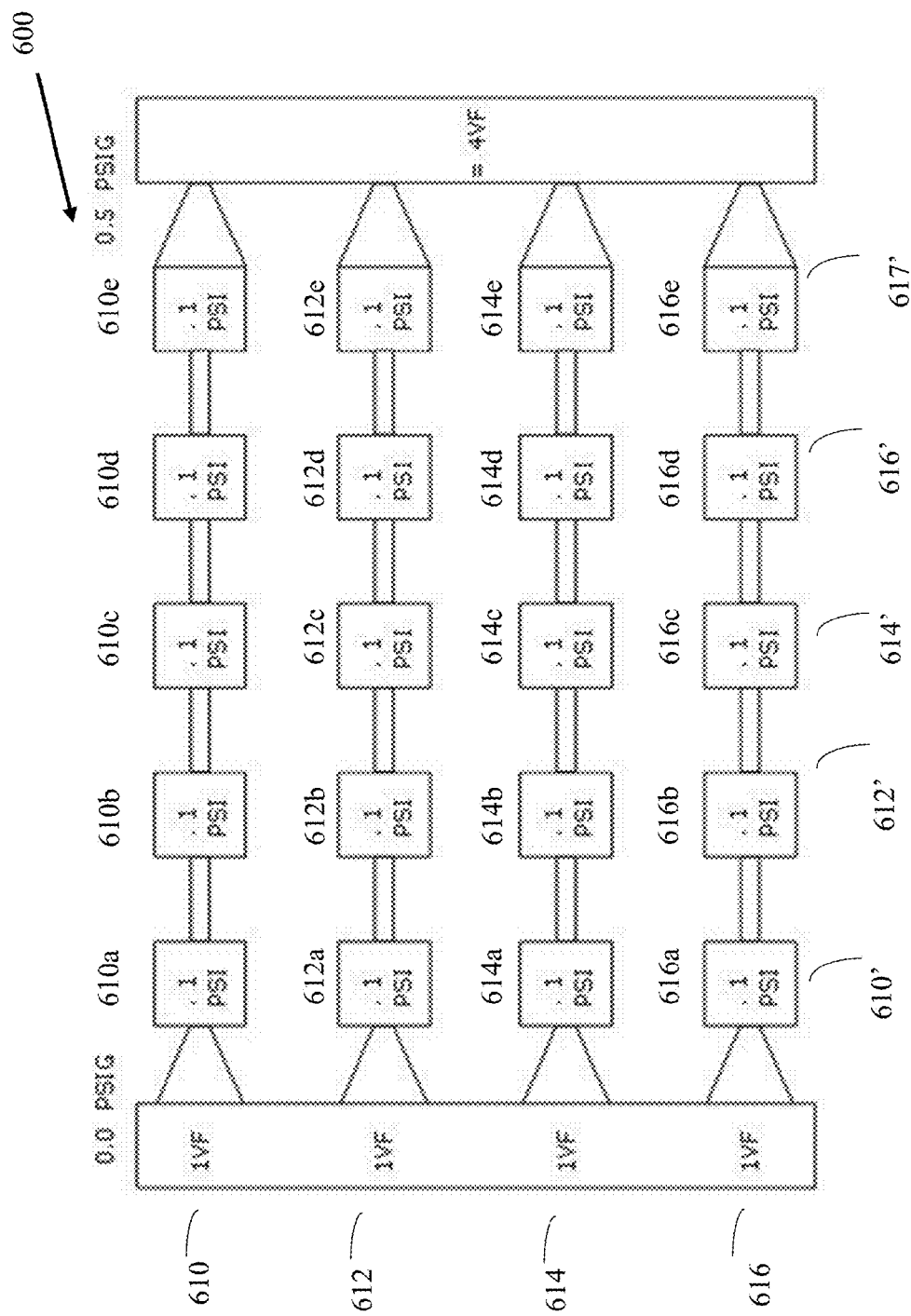
FIG. 6 is a block diagram of micro pumps arranged in an exemplary grid configuration.

Referring now to FIG. 6, rows 610-616 and columns 610'-616' and column 617' of module layer stacks (which can also be called micro pump stacks) 610a-610e, 612a-612e, 614a-614e, and 616a-616e are shown connected in a grid configuration 600. The module layer stacks in each row 610, 612, 614, 616 are connected in series. The rows 610-616 of module layer stacks 610a-610e, 612a-612e, 614a-614e, and 616a-616e are connected in parallel via a common input 620 and a common output 622.

Effectively, the serially connected stacks in each row can provide a total pressure substantially equal the sum of the individual stack pressures. In the example shown in the figure, if each stack has a pressure of 0.1 psi and each row includes five stacks, then a total pressure of 0.5 psi is effected by each row, and which is also the total pressure of the grid 600. The grid 600 has a total flow rate that is four times the flow rate of each row of stacks.

In the example shown in the figure, each row of stack has a flow rate of 1 volume flow (vF). The grid includes four parallel-connected rows, leading to a total flow rate of 4 vF. To achieve a desired pressure and a desired flow rate, a grid similar to the grid 600 can be constructed by choosing the number of stacks to be serially connected and the number of rows to be connected in parallel.

Alternatively, another series configuration has a common plenum disposed between each stage of a grouping of parallel pumps. This configuration would tend to equalize discharge pressures and thus input pressure at the next stage. In some implementations, the stacks are relatively small and many of them can be fabricated in a small area. The plumbing and wiring of the grid can be done at the time of fabrication of the individual stacks and can be done in a cost effective manner.

Example Applications

As described above, air can be used for an electrochemical reaction and cooling, e.g., in fuel cells. Generally, the amount of air used for cooling is many times more than for the reaction.

Figure 7:
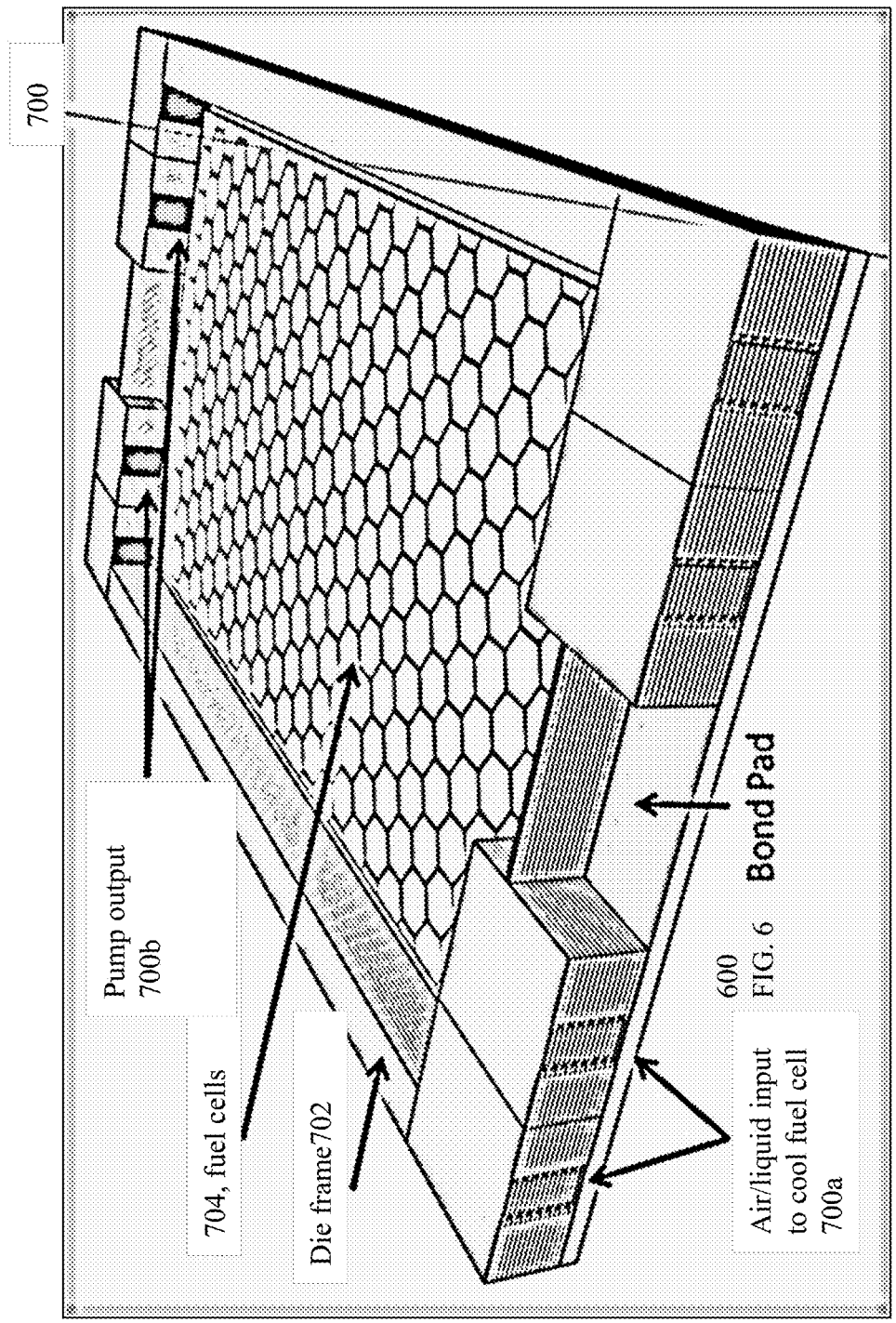
FIG. 7 is a perspective view of micro pumps integrated in a die frame.

Referring to FIG. 7, a fuel cell with an integrated micro pump system 700 with fluid inputs 700a and outputs 700b is shown. The micro pump system 600 (or 100 or 200) having features described above are integrated directly into a die frame 702 that contains fuel cells 704. When multiple dies frames are used, generally, there is a minimum spacing among the dies and some of this space can be used to house the micro pump systems 600 with no additional volumetric overhead to the dies. An exemplary fuel cell is disclosed in U.S. application Ser. No. 10/985,736, filed Nov. 9, 2004, now U.S. Pat. No. 7,029,779, and entitled "Fuel cell and power chip technology," the contents of which are incorporated herein by reference in their entirety.

Integrating the air pump systems can effectively divided the air moving function into many, e.g., thousands of parts, minimizing the need for blowers or fans to move the air. The micro pumps can be mass manufactural at a low cost, have small sizes and light weight, be reasonably powerful and consumes low power, allowing for the massive distribution of air movement. The micro pump systems 600 can be used any time air (or liquid) needs to be moved in a tight space.

Another such application is the cooling of electronic components like the CPU.

Figure 8A:
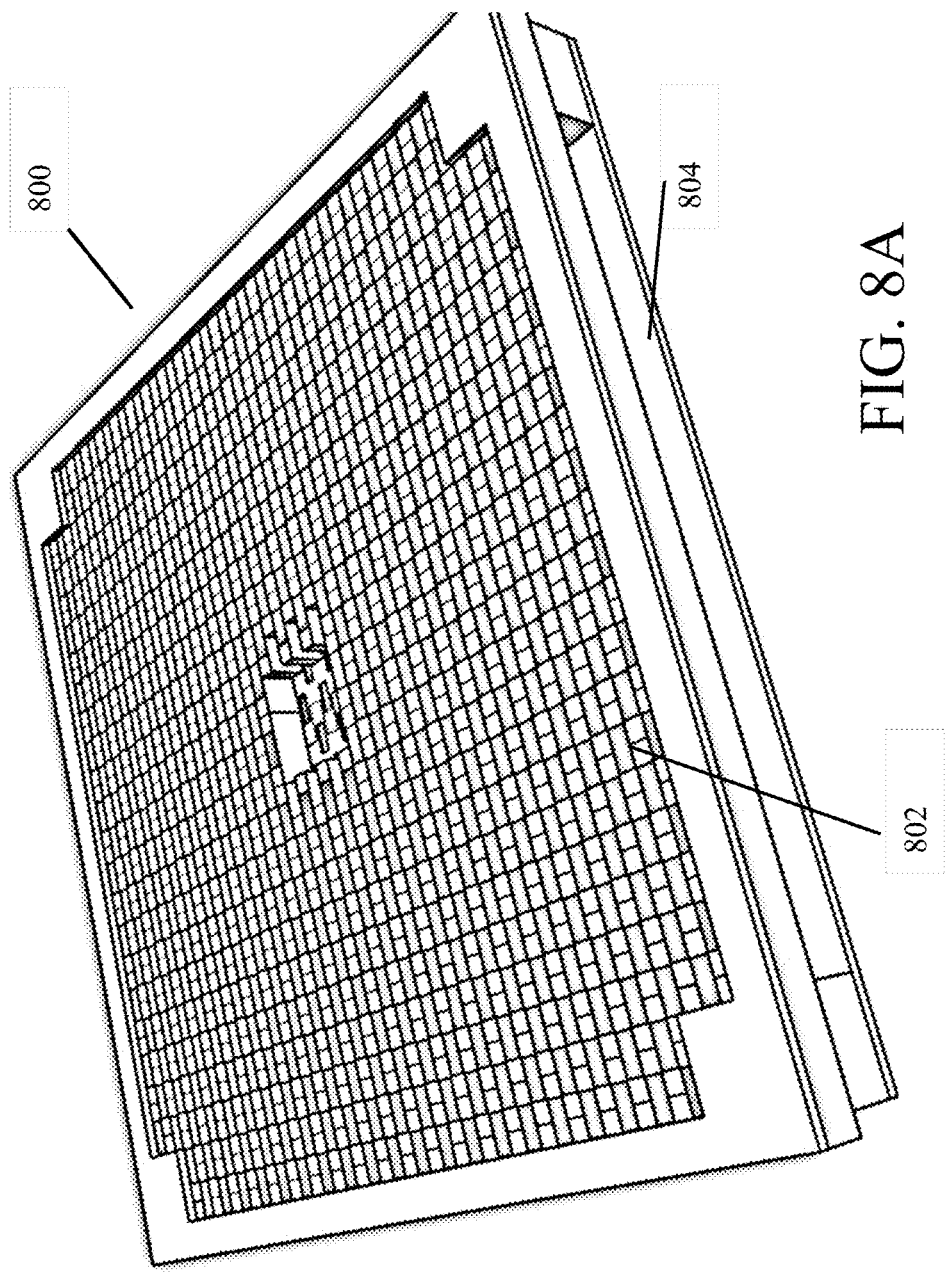
FIGS. 8A and 8B are respective top side view and bottom side view of an exemplary cooling device in a cooling arrangement.
Figure 8B:
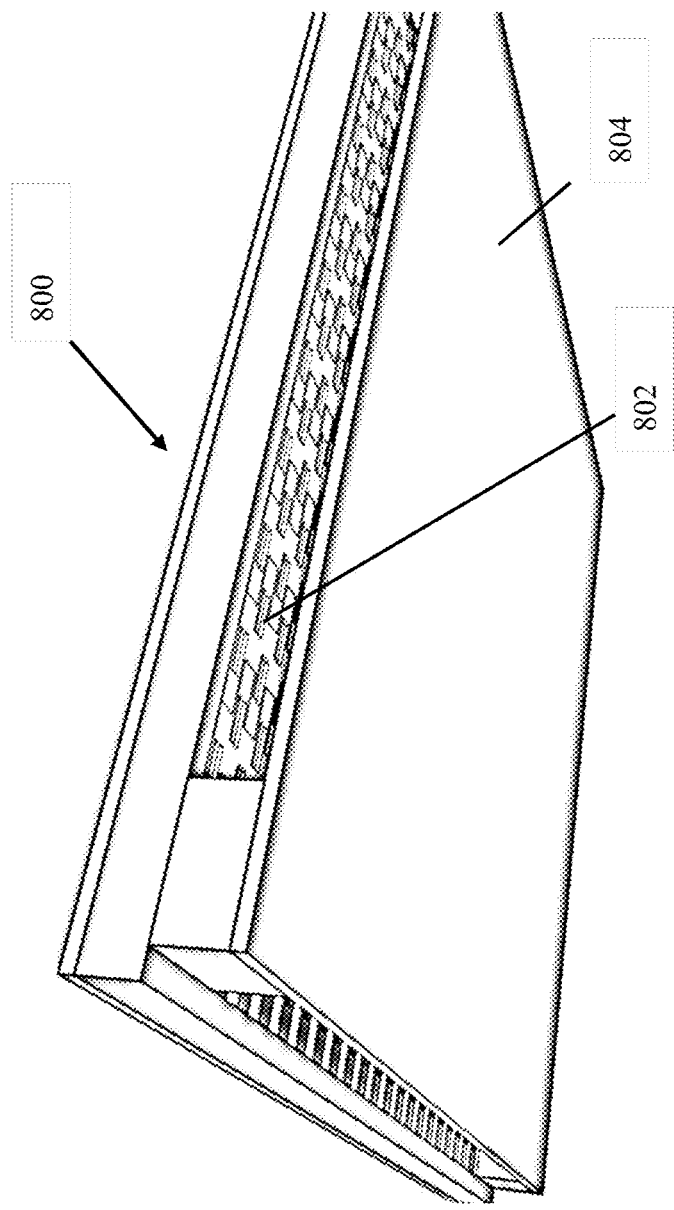

Referring now to FIGS. 8A and 8B, the micro pump (100, 200, 600) is used to cool circuits/devices, (e.g., central processor units, etc.) that run at very high temperatures, as well as, e.g., solar cells and LED lighting.

As an example, FIGS. 8A and 8B show the top side view and bottom side view of a CPU cooler 800. Instead of a large heat sink and fan arrangement, one or more layers of micro pumps 802 point directly at a cooling plate 804, for an impingement effect, that is affixed to the CPU. In some implementations, the CPU cooler 800 can remove 150 watts of heat. The cooler has a low profile and can be used in computer designs that have little available space.

The micro pump systems can be used to pump a liquid through a cooling plate fastened to the CPU to remove and transfer heat, by the liquid, to a distant location. For example, the hot liquid carrying the heat can be pumped through a radiator and additional micro pumps can be used to blow air to cool the radiator.

The micro pump systems can also blow air across a heat sink used in a traditional approach; or can be built into the heat sink. As described previously, the micro pump systems can be configured to provide an increased pressure to push air further. The micro pump systems can also be distributed throughout a host device without needing air ducts.

Referring now to FIGS. 9A and 9B, an autonomous device for treating breathing disorders 900 (device) is shown. The device 900 is a CPAP type (continuous positive airway pressure) breathing device. However, the device 900, unlike CPAP machines, is an autonomous device that is local to the nose and which provides a required amount of air flow at a required pressure to treat various breathing disorders such as obstructive sleep apnea ("OSA").

The CPAP breathing device 900 is shown in the form of a nose ring. Other arrangements are possible (see FIG. 9D). The device 900 has passages 902 for air inlets and micro pumps 600 (FIG. 6) disposed in the body 904 of the device 900, as shown. The device may also contain valves (See FIGS. 10 AND 10A-10F) to provide for exhalation. The ends 904a, 904b of the device 900, which fit into the nose of a user, provide airflow via passages 905a, 905b, and sealing and are connected via a ring portion 903 within which can be disposed a power source, e.g., battery (not shown).

As the micro pump systems are small and can move a significant amount of air, the micro pump system is built into the device 900, e.g., to provide relief to many people who have sleep apnea or obstructive breathing disorder (OBD). The device 900 can be a self-contained device that has a small size (e.g., fitting under the nose) and a light weight (e.g., as light as a few grams), and can be operated using batteries.

In some implementations, the device 900 can include exhalation valves (discussed below) whereas in other implementations the exhalation valves may be omitted.

In some implementations, the device 900 can be rechargeable, e.g., the batteries can be recharged. In others the device can be disposable. A user can wear the device at night and throw it away each day. Alternative arrangements are possible such as the use of air-metal batteries in the devices. The air-metal batteries, (e.g., air-zinc) are activated and last for a period of time, and which thereafter are disposed of.

Device 900 is configured to fit into a user's nose and supplies pressurized air flow from the micro pump 600 (or 100, 200) built into the ring. The device 900 thus does not require hoses or wires to another device (e.g., a machine) and the device uses a self-contained power source, e.g., a battery that is configured to operate for about a full-night's sleep, e.g., about eight hours or so. The device 900 does not need straps. The device can be configured to stop blowing air into a user's nose when a user is exhaling or when a user is in a pause state just prior to inhaling. The device 900 has an exhalation valve that eliminates exhalation resistance (fighting against oncoming air or cutting off the end of exhalation prematurely).

The device 900 can sense pressure to turn on and off the micro air pumps. The device 900 senses pressure on every breath and at different points in the breathing cycle to configure operation of the micro air pumps to close the exhalation valve at the "end" of the exhalation cycle. This device responds to the user on a breath by breath basis.

The device 900 is small, light-weight and fits under a use's nose, making a seal in the user's nose to hold the device in place. The device can provide proper pressure for apnea treatment during a pause period and proper hypopnea pressure range during an inhalation period. The device 900 can be disposable, thus would not require cleaning, can be low cost. Moreover, due to its relative comfort compared to existing CPAP machines, the device 900 promotes compliance as the device is comfortable, require no straps, masks or tethers.

Figure 9C:
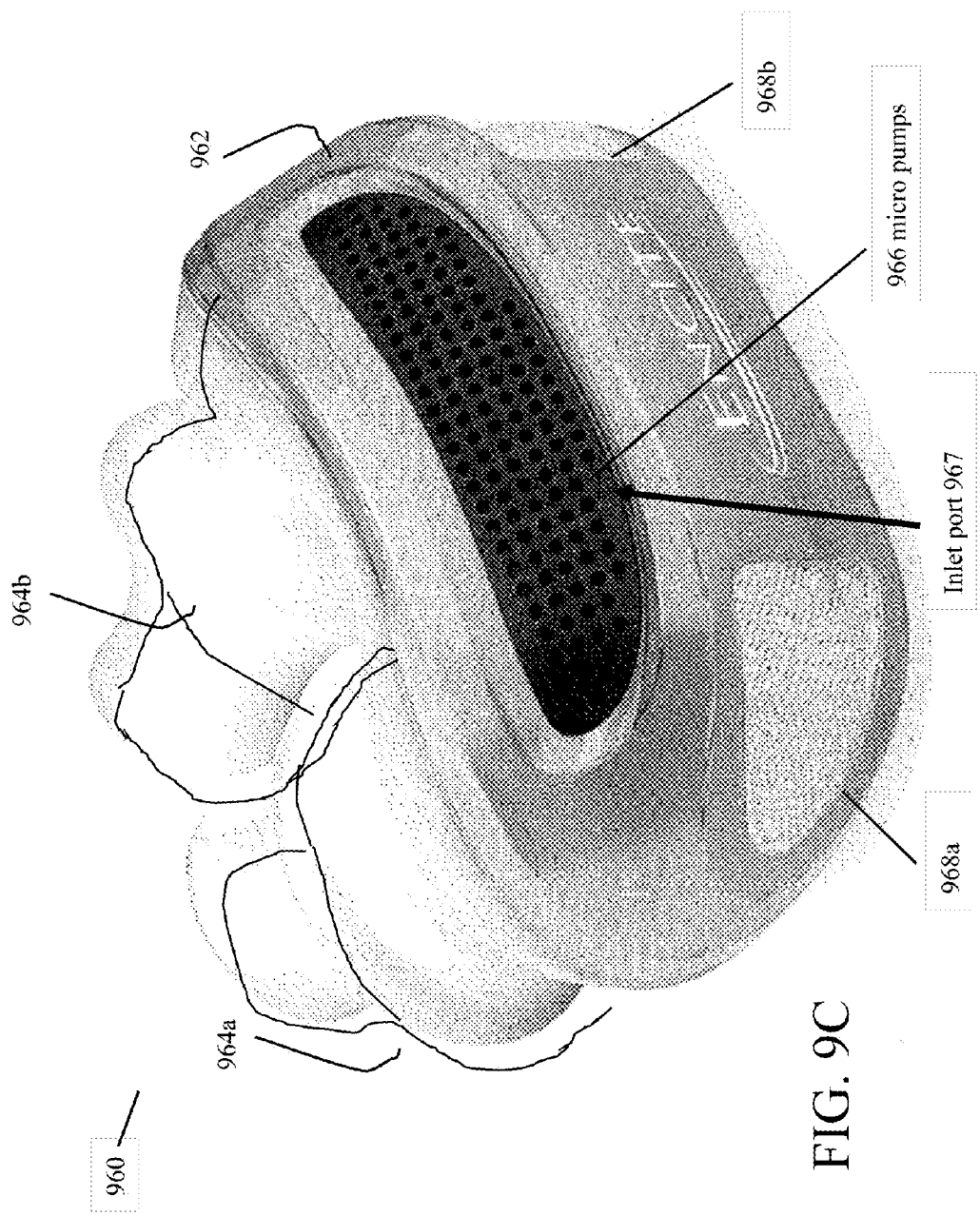
FIG. 9C is a perspective view of an alternative airway pressure breathing device.

Referring now to FIG. 9C, a conceptual view of an alternative configuration for a CPAP device 960 is shown. In this configuration, the CPAP device 960 includes a body 962 that houses a micro pumps 600 here having 57 component-pump elements denoted as 966, and an exhalation valve (see FIGS. 10A-10F). The CPAP device 960 has cushioned plugs 964a, 964b with air passages through the plugs that provide a nasal interface. The cushioned plugs are made of a generally rubbery material that make a tight fit when inserted into a user's nostrils. The CPAP device 960 has one or as shown two outlets 968a, 968b for exhilaration of air.

Figure 10:
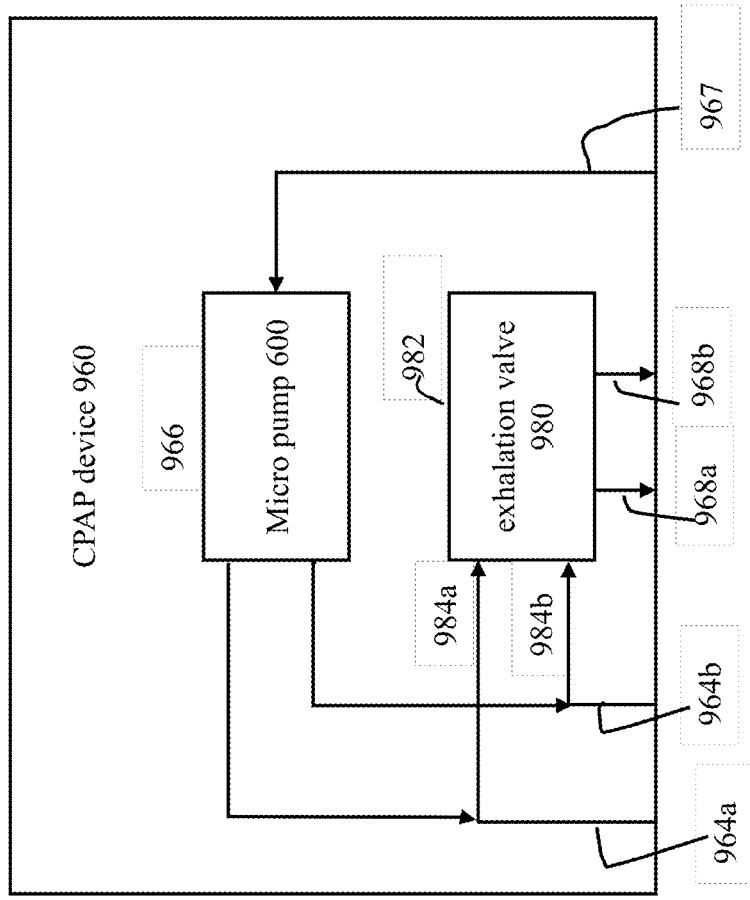
FIG. 10 is a block diagram of a CPAP (continuous positive airway pressure) breathing device.
Figure 10E:
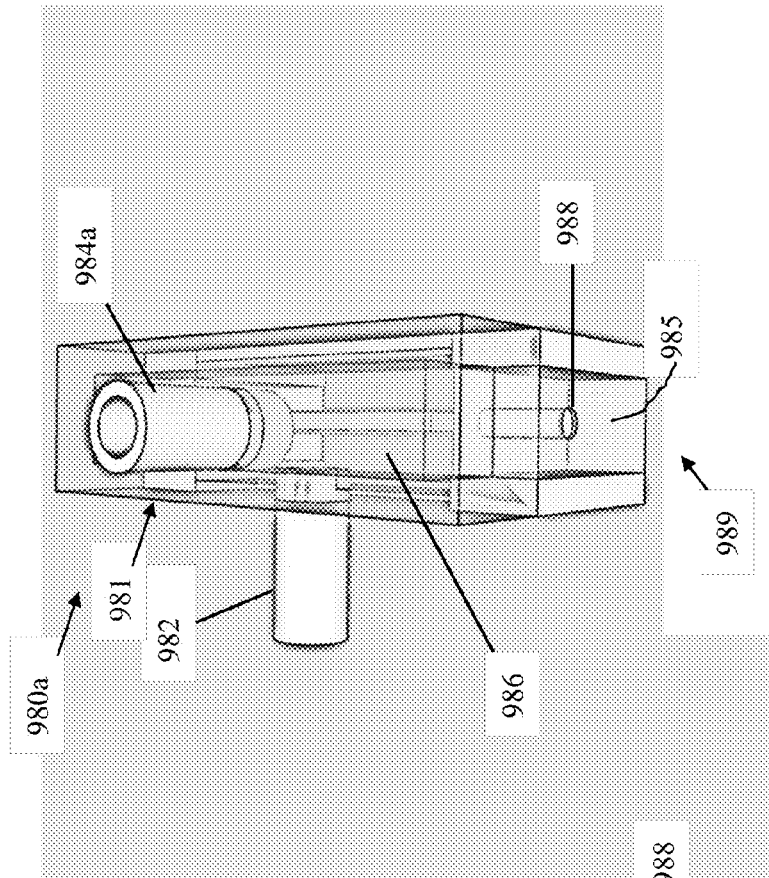
Figure 10F:
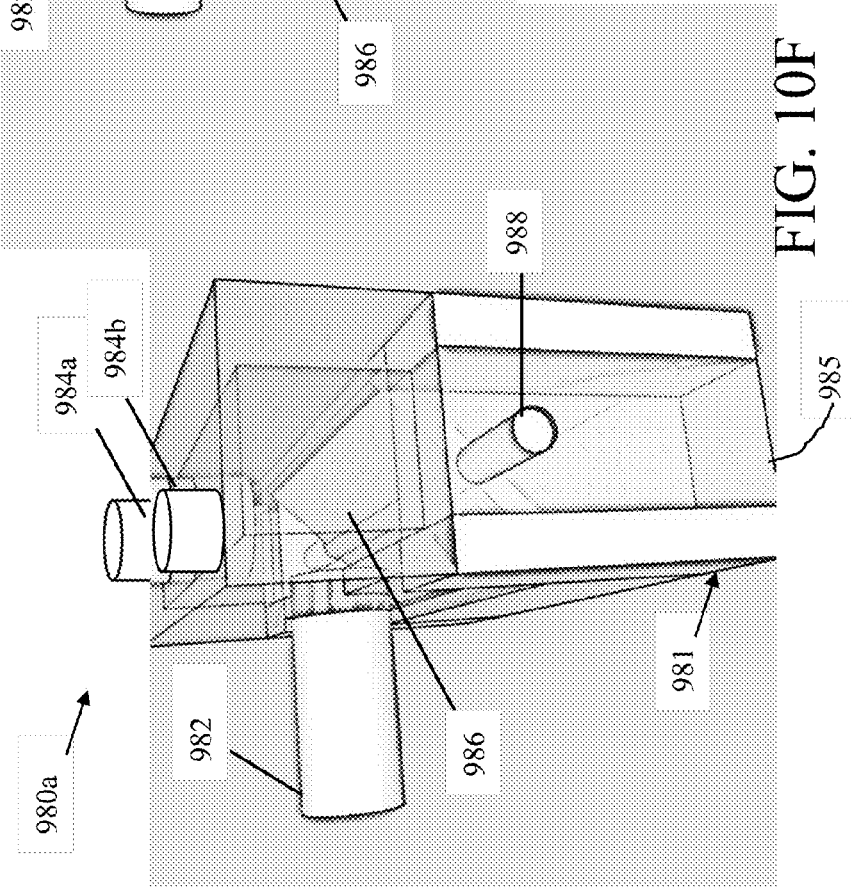

Referring now to FIG. 10, a schematic, e.g., of the configurations shown in FIGS. 9A-9C, an exhalation valve 980 coupled to a micro pump 600 within the CPAP device 900 or 960 (pumps 966). The exhalation valve 980 is coupled between the micro pumps 600 (100 or 200 as well)

and inlets 964a, 964b and outlets 968a, 968b of the device 900, as shown. The exhalation valve 980 is of a butterfly configuration and uses air flow from the micro pumps to close the valves 980 at the end of an exhalation/beginning of pause in breathing and at the beginning of exhalation, the exhalation valve 980 opens even as the micro pumps blows air on the exhalation valves 980.

The device 900 is configured to select how much of the micro pumps' 600 air flow is needed to push the valve 980 shut. Pressure from the micro pumps 600 will hold the exhalation valve 980 shut prior to exhilaration. All of the exhalation air flow from the user is applied to the exhalation valve 980 to open the exhalation valves 980. The shape of valves' flaps may be optimized to assist the exhalation valve 980 to stay open during exhalation. In addition, weak magnetics may also be used to keep exhalation valve 980 open or closed depending on details of a design. The exhalation air from a user would generally be sufficient to overcome a minimum amount of air flow from the micro pump to keep the exhalation valves 980 closed.

Referring now to FIGS. 10A-10F, various views of a conceptual exhalation valve 980 are shown. FIGS. 10A-10F show a butterfly valve configuration that is used for the exhalation valve 980. Valve 980 is illustrated and includes a body 981, an inlet 982, ports 984a and 984b (984b shown only in the view of FIG. 10F), outlet ports 985 and a valve flap 986. The flap valve 986 is rotatable about an axial member 988 to open and close a passageway between the ports 984a, 984b and outlet port 985, denoted by the large arrow 989. The micro pump 600 applies air through inlet 982 to close the flap valve 986. In the context of FIG. 10 and FIG. 9C, the inlet 982 is coupled to an output of the micro pump, the ports 984a, 984b are coupled to the plugs 964a, 964b (with air passages) and the outlet is coupled to one or both of the outlets 968a, 968b.

Figure 11A:
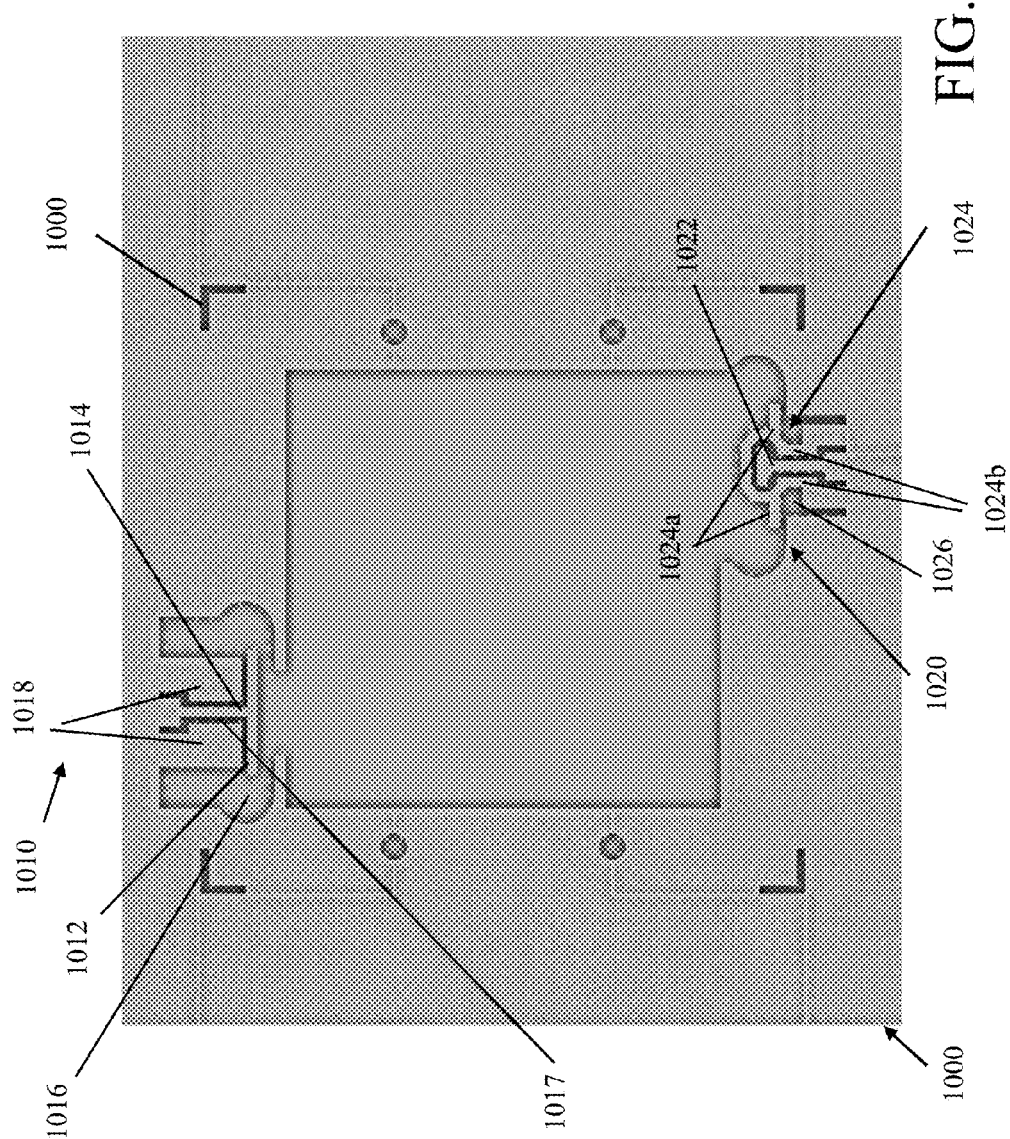
FIGS. 11A and 11B show details of exemplary sliding "T" and "omega" valves.
Figure 11B:
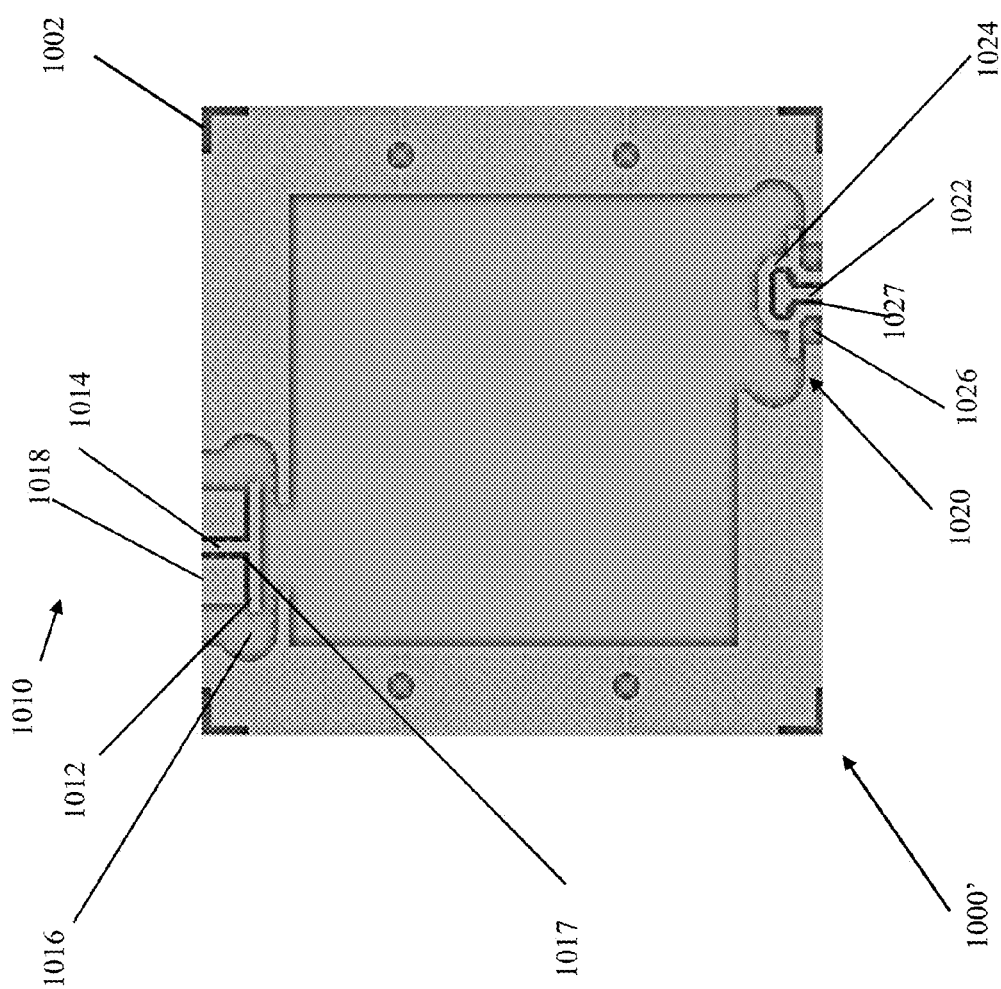

Referring now to FIGS. 11A and 11B details of exemplary a sliding valve 1010 (a "T valve") used on output ports and a sliding valve 1020 (an "omega valve") used on input ports to the chambers e.g., 209 of the micro pump, e.g., 200 (FIG. 2B).

Recalling that the chamber 209 is produced from the pump body 204 and membranes 206 (FIG. 2B) (or end walls of the pump body). In FIG. 11A, a portion of the material 1000 that is used to produce the pump body 204 provides the T valve 1010 at what would be an output port of a micro pump chamber. The T valve 1010 includes a flat member 1012 that provides a valve to close off the output port and with the flat member 1012 connected to a stem member 1014 that resides in a compartment 1017 formed from regions 1018. Outlets from the chamber are provided by regions 1016.

In FIG. 11A, another portion of the material 1000 that is used to produce the pump body 204 provide the omega valve 1020 at what would be an input port of a micro pump chamber. The omega valve 1020 includes a piston, like member 1022 that provides a stop for the omega shaped member 1024 that is somewhat semi-circular with horizontal arms 1024a that provides a valve to close off the input port and with the omega shaped member 1024 having vertical arms 1024b. The omega shaped member is confined to the region (not referenced) form between the piston member 1022 and the omega member 1024 by the piston like member 1022. Inlets from the chamber are provided by regions 1026.

Referring now to FIG. 11B the etched body 1000' has the sliding valve 1010 ("T valve") on output ports and the sliding valve 1020 ("omega valve") on input ports and which are formed by removing excess material from the material of the body guided by the etch lines 1002, as shown, leaving each of the sliding valves 1010 and 1020 to move freely within very confined regions, according to pressure applied to the chamber but not being free to move outside of the confined regions. The T valve 1010 has the flat member 1012 close off the output port, and is confined in the region defined by 1016 and 1017, whereas the mega valve 1020 is confined by the region 1026 and region 1027.

Figure 11C:
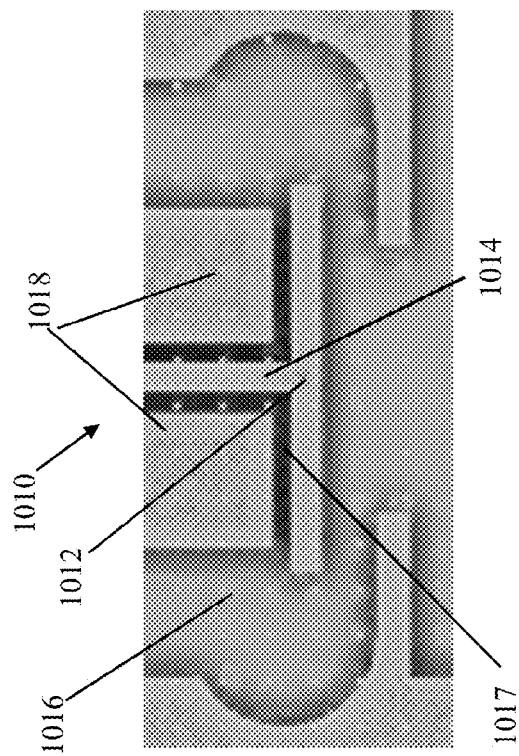
FIGS. 11C and 11D are blowup views showing details of the exemplary sliding "T" valve and "omega" valve, respectively.
Figure 11D:
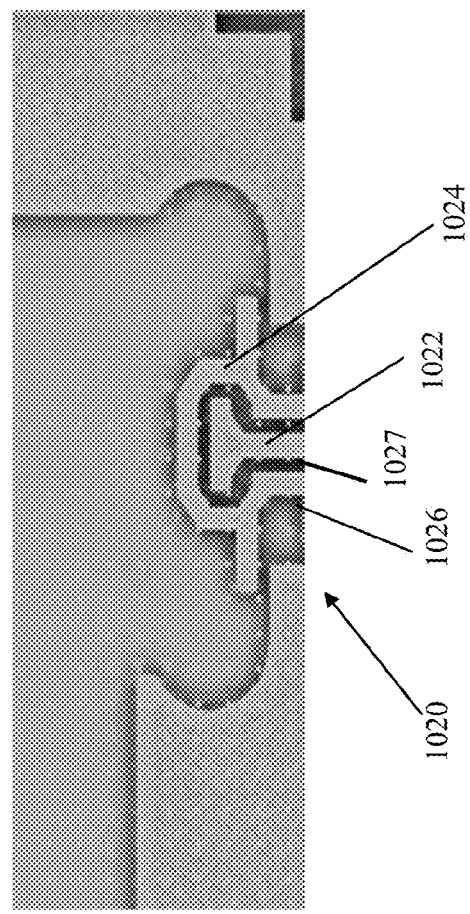

FIGS. 11C and 11D show the sliding valve 1010 ("T valve") on output ports and the sliding valve 1020 ("omega valve") on input ports at a higher magnification.

In some implementations, the micro pump systems can also be used to sense distance between membranes by measuring capacitance between the membranes. The micro pumps include electrodes, each pair of which forming an electrostatic actuator, which is effectively a variable capacitor having two conductive plates, i.e., the electrodes, spaced apart at some distance. When a voltage is applied across the two electrodes, the electrodes move towards or away from each other. As the distance between the electrodes changes, so does the capacitance. The capacitance increases as the electrodes move closer and decreases as the electrodes move apart. Accordingly, the capacitance between a pair of electrodes can provide information about the distance between the pair.

In some implementations, the information can be applied to determining a number of parameters of the system. For example, quantities including pressure, volume, flow rate, and density can be measured.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein. Other embodiments are within the scope of the following claims.

What is claimed is:

1. A micro-pump comprising:
a pump body having walls providing an enclosed pump chamber that is compartmentalized into plural compartments, with at least one of the walls of the pump chamber having a plurality of inlet ports providing fluid ingress into corresponding ones of the plural compartments of the pump chamber and a plurality of outlet ports providing fluid egress from corresponding ones of the plural compartments of the pump chamber;
a plurality of membranes disposed in the pump chamber, with the plurality of membranes having a pair of opposing major surfaces, the plurality of membranes anchored between the walls of the pump body, and which membranes compartmentalize the pump chamber into the plural compartments; and
a plurality of electrodes, with a first pair of the plurality of electrodes disposed on a pair of opposing walls of the pump body, and remaining ones of the plurality of electrodes disposed on a first one of the opposing major surfaces of each of the plurality of membranes.

2. The micro-pump of claim 1 wherein the plurality of inlets and the plurality of outlets are on the same wall of the pump body.

3. The micro-pump of claim 1 wherein the plurality of inlets and the plurality of outlets are on the same wall of the pump body, and the plurality of inlets have a first set of connections to a source and the plurality of outlets have a second, different set of connections to a sink and with the plurality of outlets isolated from the first set of connections.

4. The micro-pump of claim 1 wherein the plurality of inlets and the plurality of outlets are on opposing walls of the pump body.

5. The micro-pump of claim 1 further comprising:
a plurality of valves, a first portion of the plurality of valves being inlet valves and disposed adjacent the first plurality of inlets and a second portion of the plurality of valves being outlet valves and disposed adjacent the plurality of outlets.

6. The micro-pump of claim 1 further comprising:
a plurality of valves, with the valve being either flap-type valves and/or sliding-type valves.

7. The micro-pump of claim 1 further comprising:
a drive circuit configurable to produce a set of electrical signals to apply to the electrodes to cause the plurality of membranes disposed in the pump chamber to deflect according to polarities of voltages applied to adjacent sets of the plurality of electrodes.

8. The micro-pump of claim 7 wherein the set of electrical signals cause a first one of the plural compartments to compress and cause at least one immediately adjacent one of the plural compartments to expand substantially simultaneously.

9. The micro-pump of claim 1 further comprising a drive circuit to produce waveforms to apply to the electrodes.

10. A micro-pump comprising:
first and second micro-pump end modules each comprising:
a pump body portion, and
a membrane supported on the pump body, the membrane having a pair of major opposing surfaces and an electrically conductive electrode on one of the major surfaces thereof, with each pump body portion and each membrane portion providing a respective pump end compartment, with each of the first and second micro-pump end modules having at least an inlet port providing fluid ingress into the respective pump compartment and an outlet port providing fluid egress from the respective pump compartment;
at least a third micro-pump module that is in a stack between the first and second micro-pump end modules, the at least third micro-pump module comprising:
a pump body portion;
a membrane supported on the pump body portion, the membrane having a pair of major opposing surfaces and an electrically conductive electrode on one of the major surfaces thereof, with the at least third micro-pump module sandwiched in the stack between the first and second micro-pump end modules, with the stack of the first and second micro-pump end modules and the at least third micro-pump module providing a chamber that is compartmentalized by membranes of the first, second and at least third micro-pump modules.

11. The micro-pump of claim 10 wherein the inlet port and the outlet port of each module are on a same wall of the pump body, and the micro pump further comprises electronic drive circuitry.

12. The micro-pump of claim 10 wherein inlet ports and outlet ports of the first, second, and third modules are on the same wall of the pump body, and the inlet ports have a first set of connections to a source and the outlet ports have a second, different set of connections to a sink and with the outlet ports isolated from the first set of connections.

13. The micro-pump of claim 10 wherein the inlet and the outlet of each module are on opposing walls of the pump body.

14. The micro-pump of claim 10 further comprising a plurality of valves, with a first portion of valves being inlet valves disposed adjacent the inlet ports and, with a second portion of valves being inlet valves disposed adjacent the outlet ports.

15. The micro-pump of claim 10 wherein the valves are flap valves having a beam member and a stop.

16. A cooling device for an electrical component, the cooling device comprising:
a micro-pump comprising:
a pump body having plural walls forming a pump chamber, the pump chamber having a plurality of compartments, with the pump chamber having a plurality of inlet ports providing fluid ingress into respective compartments of the pump chamber and a plurality of outlet ports providing fluid egress from the respective compartments of the pump chamber, and a plurality of membranes disposed in the pump chamber, with the plurality of membranes anchored by walls of the pump body and providing the plurality of compartments, and a plurality of electrodes, with a first pair of the plurality of electrodes disposed on a second different pair of opposing walls of the pump body, and remaining electrodes disposed on corresponding surfaces of the membranes;
a heat plate having a first surface configured to attach to the electrical component and a second surface that is in thermal communication with the micro-pump.

17. The cooling device of claim 16 wherein the micro-pump is connected to the heat plate.

18. The cooling device of claim 16 wherein end ones of the compartments have a corresponding wall of the pump body and one of the third plurality of membranes providing the end compartments and with intermediate ones of the compartments having a pair of membranes providing the intermediate compartments.

19. An airway pressure breathing device comprises:
a body having air passages through the body terminating in a pair of end portions, with each end portion having at least one outlet in a first surface of the end portion; and
a micro pump supported in a portion of the body, the micro pump configured to pump ambient air through the air passages in the body to the end portions, with the micro pump comprising:
plural micro-pump modules disposed in a stack, each micro-pump module comprising:
a pump body having an inlet and an outlet; and
a membrane having an electrically conductive electrode on one of a pair of major surfaces of the membrane;
a pair of pump end modules each comprising:
a pump body; and
an electrically conductive electrode, with the pair of pump end modules disposed on ends of the stack, with a pump body of each micro-pump module spaced from a pump body of an adjacent intermediate micro pump module by a membrane of the adjacent micro-pump module.

20. The airway pressure breathing device of claim 19 further comprising:
a battery to provide a power source for the micro pump, the battery supported on the body.

21. The airway pressure breathing device of claim 19, further comprising:
a butterfly type valve disposed in fluid communication with the micro pump.

22. The airway pressure breathing device of claim 19, further comprising:
a pair of plugs having air passages at the end portions of the body, which pair of plugs are configured to be inserted into a pair of nostrils of a user.

23. The airway pressure breathing device of claim 19, wherein the end portions comprise a nasal interface that snugly fits within nostrils of a user.

24. The airway pressure breathing device of claim 19, further comprising:
a nasal interface at the end portions, which nasal interface configured to snugly fit within nostrils of a user.

25. A micro-pump comprising:
a pump body having a pump chamber compartmentalized into plural compartments, with each compartment defined in part by walls of the pump body, and having an inlet valve on a first pump body wall to provide controlled fluid ingress into the respective compartment and an outlet valve a second pump body wall providing controlled fluid egress from the respective compartment;
plural membranes disposed in the pump chamber, with the plural membranes anchored between the walls of the pump body, with adjacent ones of the plural membranes and the walls of the pump body enclosing respective ones of the plural compartments; and
a plurality of electrodes, with each one of the plurality of membranes carrying a corresponding one of the plurality of electrodes on a major surface of the membrane.

26. The micro-pump of claim 25 wherein adjacent valves on inlets on the first pump body wall are staggered relative to each other and adjacent valves on outlets on the second pump body wall are staggered relative to each other.

27. The micro-pump of claim 25 wherein the pump body is comprised of plural pump body module layers, each of the pump body module layers supporting one of the plural membranes and corresponding electrode, with the pump body module layers arranged in a stack to provide the pump chamber compartmentalized into the plural compartments.

28. The micro-pump of claim 25 wherein the outlet values are sliding valves.

29. The micro-pump of claim 25 wherein each outlet valve has a valve member that includes a stem portion perpendicularly connected to a flap portion, and with a portion of the second pump body wall having a passage through the second body wall, and having in the passage a pair of spaced body wall regions that are spaced from each other by a first gap and spaced from wall portions of the pump body by a pair of second gaps, with the stem portion within the first gap between the pair of spaced wall regions, and with the flap portion confined within the passage by the flap portion having a width that is greater than a width of an external opening in the pump body provided by the passage.

30. The micro-pump of claim 25 further comprising:
a drive circuit to produce electrical signals to apply to the electrodes.

31. The micro-pump of claim 30 wherein the drive circuit is configured to produce the electrical signals to apply to the electrodes to cause the plural membranes to deflect according to polarities of voltages applied to the plurality of electrodes.

32. The micro-pump of claim 30 wherein the drive circuit is configured to produce the electrical signals to apply to the electrodes to cause a first one of the plural compartments to compress and cause at least one adjacent one of the plural compartments to expand substantially simultaneously.

33. The micro-pump of claim 25 wherein the inlet values are sliding valves.

34. The micro-pump of claim 25 wherein each inlet valve has a somewhat semi-circular portion, a pair of end-portions coupled to ends of the semi-circular portion and a pair of vertical arm portions relative to the pair of end portions, and a piston-like member having a stem portion and a head portion, the piston-like member supported on a corresponding one of the membrane layers, with a portion of the first pump body wall having a passage through the first body wall, and having in the passage the piston-like member, with a width defined by extremities of the end-portions being wider than a width of a portion of the passage that provides an external egress in the first body wall, and a width defined by a portion of the piston member being wider than a portion defined by interior surface of the semi-circular portion.

35. The micro-pump of claim 25 further comprising:
a first electrode disposed on a first one of a pair of opposing walls of the pump body; and
a second electrode disposed on a second one of the pair of opposing walls of the pump body.

36. A micro-pump comprising:
plural micro-pump modules disposed in a stack, each micro-pump module comprising:
a pump body having an inlet and an outlet; and
a membrane having an electrically conductive electrode on one of a pair of major surfaces of the membrane;
a pair of pump end modules each comprising a pump body and an electrically conductive electrode with the pair of pump end modules disposed on ends of the stack, with a pump body of each micro-pump module spaced from a pump body of an adjacent intermediate micro pump module by a membrane of the adjacent micro-pump module.

37. The micro-pump of claim 36 further comprising:
an electronic drive circuit having conductors electrically coupled to the electrically conductive electrode on major surface of the membrane of each of the plural micro-pump modules and the electrically conductive electrodes on the pair of pump end modules.

38. The micro-pump of claim 37 further comprising a plurality of inlet valves disposed in inlets and a plurality of outlet valves disposed in outlets.

39. The micro-pump of claim 37 wherein the inlet and outlet valves are flap valves having a beam member and a stop.

* * * * *